United States Patent
Bokil

(10) Patent No.: US 9,956,419 B2
(45) Date of Patent: May 1, 2018

(54) SYSTEMS AND METHODS FOR ANALYZING ELECTRICAL STIMULATION AND SELECTING OR MANIPULATING VOLUMES OF ACTIVATION

(71) Applicant: Boston Scientific Neuromodulation Corporation, Valencia, CA (US)

(72) Inventor: Hemant Bokil, Santa Monica, CA (US)

(73) Assignee: Boston Scientific Neuromodulation Corporation, Valencia, CA (US)

(*) Notice: Subject to any disclaimer, the term of this patent is extended or adjusted under 35 U.S.C. 154(b) by 86 days.

(21) Appl. No.: 15/163,581

(22) Filed: May 24, 2016

(65) Prior Publication Data

US 2016/0346557 A1 Dec. 1, 2016

Related U.S. Application Data

(60) Provisional application No. 62/166,569, filed on May 26, 2015.

(51) Int. Cl.
- *A61N 1/372* (2006.01)
- *A61N 1/36* (2006.01)
- *A61N 1/05* (2006.01)

(52) U.S. Cl.
CPC ....... *A61N 1/37247* (2013.01); *A61N 1/0534* (2013.01); *A61N 1/0551* (2013.01);
(Continued)

(58) Field of Classification Search
None
See application file for complete search history.

(56) References Cited

U.S. PATENT DOCUMENTS 3,999,555 A 12/1976 Person
4,144,889 A 3/1979 Tyers et al.
(Continued)

FOREIGN PATENT DOCUMENTS

EP 1048320 11/2000
EP 1166819 1/2002
(Continued)

OTHER PUBLICATIONS

International Search Report and Written Opinion for PCT Application No. PCT/US2016/033969 dated Oct. 19, 2016.
(Continued)

*Primary Examiner* — Brian T Gedeon
(74) *Attorney, Agent, or Firm* — Lowe Graham Jones PLLC; Bruce E. Black

(57) ABSTRACT

A system for identifying potential portions of a body in which electrical stimulation to treat a condition or disorder affects at least one symptom of the condition or disorder, stimulation effect, or side effect performs the following acts: obtaining, for each of multiple stimulation instances, an estimation of a region of the body stimulated during the stimulation instance and a score for each of at least one symptom, stimulation effect, or stimulation side effect; and determining, for each of multiple portions of the body using the scores and the estimates in a permutation test, a likelihood that stimulation of that portion of the body affects at least one symptom, stimulation effect, or stimulation side effect. In other embodiments, the system sets up a relationship between the outcomes of stimulation and influence of a particular part of the body on the outcome, and derives this influence using a pseudoinverse.

9 Claims, 7 Drawing Sheets

(52) U.S. Cl.
CPC ....... *A61N 1/3605* (2013.01); *A61N 1/36135* (2013.01); *A61N 1/36182* (2013.01)

(56) References Cited

U.S. PATENT DOCUMENTS

| | | | |
|---|---|---|---|
| 4,177,818 A | 12/1979 | De Pedro | |
| 4,341,221 A | 7/1982 | Testerman | |
| 4,378,797 A | 4/1983 | Osterholm | |
| 4,445,500 A | 5/1984 | Osterholm | |
| 4,735,208 A | 4/1988 | Wyler et al. | |
| 4,765,341 A | 8/1988 | Mower et al. | |
| 4,841,973 A | 6/1989 | Stecker | |
| 5,067,495 A | 11/1991 | Brehm | |
| 5,099,846 A | 3/1992 | Hardy | |
| 5,222,494 A | 6/1993 | Baker, Jr. | |
| 5,255,693 A | 10/1993 | Dutcher | |
| 5,259,387 A | 11/1993 | dePinto | |
| 5,304,206 A | 4/1994 | Baker, Jr. et al. | |
| 5,344,438 A | 9/1994 | Testerman et al. | |
| 5,361,763 A | 11/1994 | Kao et al. | |
| 5,452,407 A | 9/1995 | Crook | |
| 5,560,360 A | 10/1996 | Filler et al. | |
| 5,565,949 A | 10/1996 | Kasha, Jr. | |
| 5,593,427 A | 1/1997 | Gliner et al. | |
| 5,601,612 A | 2/1997 | Gliner et al. | |
| 5,607,454 A | 3/1997 | Cameron et al. | |
| 5,620,470 A | 4/1997 | Gliner et al. | |
| 5,651,767 A | 7/1997 | Schulmann | |
| 5,711,316 A | 1/1998 | Elsberry et al. | |
| 5,713,922 A | 2/1998 | King | |
| 5,716,377 A | 2/1998 | Rise et al. | |
| 5,724,985 A | 3/1998 | Snell et al. | |
| 5,749,904 A | 5/1998 | Gliner et al. | |
| 5,749,905 A | 5/1998 | Gliner et al. | |
| 5,776,170 A | 7/1998 | MacDonald et al. | |
| 5,782,762 A | 7/1998 | Vining | |
| 5,843,148 A | 12/1998 | Gijsbers et al. | |
| 5,859,922 A | 1/1999 | Hoffmann | |
| 5,868,740 A | 2/1999 | LeVeen et al. | |
| 5,897,583 A | 4/1999 | Meyer et al. | |
| 5,910,804 A | 6/1999 | Fortenbery et al. | |
| 5,925,070 A | 7/1999 | King et al. | |
| 5,938,688 A | 8/1999 | Schiff | |
| 5,938,690 A | 8/1999 | Law et al. | |
| 5,978,713 A | 11/1999 | Prutchi et al. | |
| 6,016,449 A | 1/2000 | Fischell et al. | |
| 6,029,090 A | 2/2000 | Herbst | |
| 6,029,091 A | 2/2000 | de la Rama et al. | |
| 6,050,992 A | 4/2000 | Nichols | |
| 6,058,331 A | 5/2000 | King | |
| 6,066,163 A | 5/2000 | John | |
| 6,083,162 A | 7/2000 | Vining | |
| 6,094,598 A | 7/2000 | Elsberry et al. | |
| 6,096,756 A | 8/2000 | Crain et al. | |
| 6,106,460 A | 8/2000 | Panescu et al. | |
| 6,109,269 A | 8/2000 | Rise et al. | |
| 6,128,538 A | 10/2000 | Fischell et al. | |
| 6,129,685 A | 10/2000 | Howard, III | |
| 6,146,390 A | 11/2000 | Heilbrun et al. | |
| 6,161,044 A | 12/2000 | Silverstone | |
| 6,167,311 A | 12/2000 | Rezai | |
| 6,192,266 B1 | 2/2001 | Dupree et al. | |
| 6,205,361 B1 | 3/2001 | Kuzma | |
| 6,208,881 B1 | 3/2001 | Champeau | |
| 6,240,308 B1 | 5/2001 | Hardy et al. | |
| 6,246,912 B1 | 6/2001 | Sluijter et al. | |
| 6,253,109 B1 | 6/2001 | Gielen | |
| 6,289,239 B1 | 9/2001 | Panescu et al. | |
| 6,301,492 B1 | 10/2001 | Zonenshayn | |
| 6,310,619 B1 | 10/2001 | Rice | |
| 6,319,241 B1 | 11/2001 | King | |
| 6,336,899 B1 | 1/2002 | Yamazaki | |
| 6,343,226 B1 | 1/2002 | Sunde et al. | |
| 6,351,675 B1 | 2/2002 | Tholen et al. | |
| 6,353,762 B1 | 3/2002 | Baudino et al. | |
| 6,366,813 B1 | 4/2002 | Dilorenzo | |
| 6,368,331 B1 | 4/2002 | Front et al. | |
| 6,389,311 B1 | 5/2002 | Whayne et al. | |
| 6,393,325 B1 | 5/2002 | Mann et al. | |
| 6,421,566 B1 | 7/2002 | Holsheimer | |
| 6,435,878 B1 | 8/2002 | Reynolds et al. | |
| 6,442,432 B2 | 8/2002 | Lee | |
| 6,463,328 B1 | 10/2002 | John | |
| 6,491,699 B1 | 12/2002 | Henderson et al. | |
| 6,494,831 B1 | 12/2002 | Koritzinsky | |
| 6,507,759 B1 | 1/2003 | Prutchi et al. | |
| 6,510,347 B2 | 1/2003 | Borkan | |
| 6,517,480 B1 | 2/2003 | Krass | |
| 6,539,263 B1 | 3/2003 | Schiff | |
| 6,560,490 B2 | 5/2003 | Grill et al. | |
| 6,579,280 B1 | 6/2003 | Kovach et al. | |
| 6,600,956 B2 | 7/2003 | Maschino et al. | |
| 6,606,523 B1 | 8/2003 | Jenkins | |
| 6,609,031 B1 | 8/2003 | Law et al. | |
| 6,622,048 B1 | 9/2003 | Mann et al. | |
| 6,631,297 B1 | 10/2003 | Mo | |
| 6,654,642 B2 | 11/2003 | North et al. | |
| 6,662,053 B2 | 12/2003 | Borkan | |
| 6,675,046 B2 | 1/2004 | Holsheimer | |
| 6,684,106 B2 | 1/2004 | Herbst | |
| 6,687,392 B1 | 2/2004 | Touzawa et al. | |
| 6,690,972 B2 | 2/2004 | Conley et al. | |
| 6,690,974 B2 | 2/2004 | Archer et al. | |
| 6,692,315 B1 | 2/2004 | Soumillon et al. | |
| 6,694,162 B2 | 2/2004 | Hartiep | |
| 6,694,163 B1 | 2/2004 | Vining | |
| 6,708,096 B1 | 3/2004 | Frei et al. | |
| 6,748,098 B1 | 6/2004 | Rosenfeld | |
| 6,748,276 B1 | 6/2004 | Daignault, Jr. et al. | |
| 6,778,846 B1 | 8/2004 | Martinez et al. | |
| 6,788,969 B2 | 9/2004 | Dupree et al. | |
| 6,795,737 B2 | 9/2004 | Gielen et al. | |
| 6,827,681 B2 | 12/2004 | Tanner et al. | |
| 6,830,544 B2 | 12/2004 | Tanner | |
| 6,845,267 B2 | 1/2005 | Harrison et al. | |
| 6,850,802 B2 | 2/2005 | Holsheimer | |
| 6,895,280 B2 | 5/2005 | Meadows et al. | |
| 6,909,913 B2 | 6/2005 | Vining | |
| 6,937,891 B2 | 8/2005 | Leinders et al. | |
| 6,937,903 B2 | 8/2005 | Schuler et al. | |
| 6,944,497 B2 | 9/2005 | Stypulkowski | |
| 6,944,501 B1 | 9/2005 | Pless | |
| 6,950,707 B2 | 9/2005 | Whitehurst | |
| 6,969,388 B2 | 11/2005 | Goldman et al. | |
| 7,003,349 B1 | 2/2006 | Andersson et al. | |
| 7,003,352 B1 | 2/2006 | Whitehurst | |
| 7,008,370 B2 | 3/2006 | Tanner et al. | |
| 7,008,413 B2 | 3/2006 | Kovach et al. | |
| 7,035,690 B2 | 4/2006 | Goetz | |
| 7,043,293 B1 | 5/2006 | Baura | |
| 7,047,082 B1 | 5/2006 | Schrom et al. | |
| 7,047,084 B2 | 5/2006 | Erickson et al. | |
| 7,050,857 B2 | 5/2006 | Samuelsson et al. | |
| 7,054,692 B1 | 5/2006 | Whitehurst et al. | |
| 7,136,518 B2 | 5/2006 | Griffin et al. | |
| 7,058,446 B2 | 6/2006 | Schuler et al. | |
| 7,082,333 B1 | 7/2006 | Bauhahn et al. | |
| 7,107,102 B2 | 9/2006 | Daignault et al. | |
| 7,126,000 B2 | 10/2006 | Ogawa | |
| 7,127,297 B2 | 10/2006 | Law et al. | |
| 7,136,695 B2 | 11/2006 | Pless et al. | |
| 7,142,923 B2 | 11/2006 | North et al. | |
| 7,146,219 B2 | 12/2006 | Sieracki et al. | |
| 7,146,223 B1 | 12/2006 | King | |
| 7,151,961 B1 | 12/2006 | Whitehurst | |
| 7,155,279 B2 | 12/2006 | Whitehurst | |
| 7,167,760 B2 | 1/2007 | Dawant et al. | |
| 7,177,674 B2 | 2/2007 | Echauz et al. | |
| 7,181,286 B2 | 2/2007 | Sieracki et al. | |
| 7,184,837 B2 | 2/2007 | Goetz | |
| 7,191,014 B2 | 3/2007 | Kobayashi et al. | |
| 7,209,787 B2 | 4/2007 | Dilorenzo | |
| 7,211,050 B1 | 5/2007 | Caplygin | |
| 7,216,000 B2 | 5/2007 | Sieracki et al. | |

(56) References Cited

U.S. PATENT DOCUMENTS

| | | |
|---|---|---|
| 7,217,276 B2 | 5/2007 | Henderson |
| 7,218,968 B2 | 5/2007 | Condie et al. |
| 7,228,179 B2 | 6/2007 | Campen et al. |
| 7,231,254 B2 | 6/2007 | DiLorenzo |
| 7,236,830 B2 | 6/2007 | Gliner |
| 7,239,910 B2 | 7/2007 | Tanner |
| 7,239,916 B2 | 7/2007 | Thompson et al. |
| 7,239,926 B2 | 7/2007 | Goetz |
| 7,242,984 B2 | 7/2007 | DiLorenzo |
| 7,252,090 B2 | 8/2007 | Goetz |
| 7,254,445 B2 | 8/2007 | Law et al. |
| 7,254,446 B1 | 8/2007 | Erickson |
| 7,257,447 B2 | 8/2007 | Cates et al. |
| 7,266,412 B2 | 9/2007 | Stypulkowski |
| 7,294,107 B2 | 11/2007 | Simon et al. |
| 7,295,876 B1 | 11/2007 | Erickson |
| 7,299,096 B2 | 11/2007 | Balzer et al. |
| 7,308,302 B1 | 12/2007 | Schuler et al. |
| 7,313,430 B2 | 12/2007 | Urquhart |
| 7,324,851 B1 | 1/2008 | DiLorenzo |
| 7,346,382 B2 * | 3/2008 | McIntyre ........... A61N 1/36082 600/407 |
| 7,388,974 B2 | 6/2008 | Yanagita |
| 7,463,928 B2 | 12/2008 | Lee et al. |
| 7,499,048 B2 | 3/2009 | Sieracki et al. |
| 7,505,815 B2 | 3/2009 | Lee et al. |
| 7,548,786 B2 | 6/2009 | Lee et al. |
| 7,565,199 B2 | 7/2009 | Sheffield et al. |
| 7,603,177 B2 | 10/2009 | Sieracki et al. |
| 7,617,002 B2 | 11/2009 | Goetz |
| 7,623,918 B2 | 11/2009 | Goetz |
| 7,650,184 B2 | 1/2010 | Walter |
| 7,657,319 B2 | 2/2010 | Goetz et al. |
| 7,676,273 B2 | 3/2010 | Goetz et al. |
| 7,680,526 B2 | 3/2010 | McIntyre et al. |
| 7,734,340 B2 | 6/2010 | De Ridder |
| 7,826,902 B2 | 11/2010 | Stone et al. |
| 7,848,802 B2 | 12/2010 | Goetz et al. |
| 7,860,548 B2 | 12/2010 | McIntyre et al. |
| 7,904,134 B2 | 3/2011 | McIntyre et al. |
| 7,945,105 B1 | 5/2011 | Jaenisch |
| 8,019,439 B2 | 9/2011 | Kuzma et al. |
| 8,180,601 B2 | 5/2012 | Butson et al. |
| 8,195,300 B2 | 6/2012 | Gliner et al. |
| 8,257,684 B2 | 9/2012 | Covalin et al. |
| 8,262,714 B2 | 9/2012 | Hulvershorn et al. |
| 8,379,952 B2 * | 2/2013 | McIntyre ........... A61N 1/36082 382/131 |
| 8,429,174 B2 | 4/2013 | Ramani et al. |
| 8,452,415 B2 | 5/2013 | Goetz et al. |
| 8,543,189 B2 | 9/2013 | Paitel et al. |
| 8,594,800 B2 * | 11/2013 | Butson ................. G06F 19/345 600/407 |
| 8,606,360 B2 | 12/2013 | Butson et al. |
| 8,620,452 B2 | 12/2013 | King et al. |
| 8,644,946 B2 * | 2/2014 | Butson ................. G06F 19/345 600/407 |
| 8,812,126 B2 * | 8/2014 | Butson ................. G06F 19/345 600/407 |
| 9,364,679 B2 * | 6/2016 | John ..................... A61N 1/3605 |
| 2001/0031071 A1 | 10/2001 | Nichols et al. |
| 2002/0032375 A1 | 3/2002 | Bauch et al. |
| 2002/0062143 A1 | 5/2002 | Baudino et al. |
| 2002/0087201 A1 | 7/2002 | Firlik et al. |
| 2002/0099295 A1 | 7/2002 | Gil et al. |
| 2002/0115603 A1 | 8/2002 | Whitehouse |
| 2002/0116030 A1 | 8/2002 | Rezei |
| 2002/0123780 A1 | 9/2002 | Grill et al. |
| 2002/0128694 A1 | 9/2002 | Holsheimer |
| 2002/0151939 A1 | 10/2002 | Rezai |
| 2002/0183607 A1 | 12/2002 | Bauch et al. |
| 2002/0183740 A1 | 12/2002 | Edwards et al. |
| 2002/0183817 A1 | 12/2002 | Van Venrooij et al. |
| 2003/0097159 A1 | 5/2003 | Schiff et al. |
| 2003/0149450 A1 | 8/2003 | Mayberg |
| 2003/0171791 A1 | 9/2003 | KenKnight et al. |
| 2003/0212439 A1 | 11/2003 | Schuler et al. |
| 2004/0034394 A1 | 2/2004 | Woods et al. |
| 2004/0044279 A1 | 3/2004 | Lewin et al. |
| 2004/0044378 A1 | 3/2004 | Holsheimer |
| 2004/0044379 A1 | 3/2004 | Holsheimer |
| 2004/0054297 A1 | 3/2004 | Wingeier et al. |
| 2004/0059395 A1 | 3/2004 | North et al. |
| 2004/0106916 A1 | 6/2004 | Quaid et al. |
| 2004/0133248 A1 | 7/2004 | Frei et al. |
| 2004/0152957 A1 | 8/2004 | Stivoric et al. |
| 2004/0181262 A1 | 9/2004 | Bauhahn |
| 2004/0186532 A1 | 9/2004 | Tadlock |
| 2004/0199216 A1 | 10/2004 | Lee et al. |
| 2004/0267330 A1 | 12/2004 | Lee et al. |
| 2005/0021090 A1 | 1/2005 | Schuler et al. |
| 2005/0033380 A1 | 2/2005 | Tanner et al. |
| 2005/0049649 A1 | 3/2005 | Luders et al. |
| 2005/0060001 A1 | 3/2005 | Singhal et al. |
| 2005/0060009 A1 | 3/2005 | Goetz |
| 2005/0070781 A1 | 3/2005 | Dawant et al. |
| 2005/0075689 A1 | 4/2005 | Toy et al. |
| 2005/0085714 A1 | 4/2005 | Foley et al. |
| 2005/0165294 A1 | 7/2005 | Weiss |
| 2005/0171587 A1 | 8/2005 | Daglow et al. |
| 2005/0228250 A1 | 10/2005 | Bitter et al. |
| 2005/0251061 A1 | 11/2005 | Schuler et al. |
| 2005/0261061 A1 | 11/2005 | Nguyen et al. |
| 2005/0261601 A1 | 11/2005 | Schuler et al. |
| 2005/0261747 A1 | 11/2005 | Schuler et al. |
| 2005/0267347 A1 | 12/2005 | Oster |
| 2005/0288732 A1 | 12/2005 | Schuler et al. |
| 2006/0004422 A1 | 1/2006 | De Ridder |
| 2006/0017749 A1 | 1/2006 | McIntyre et al. |
| 2006/0020292 A1 | 1/2006 | Goetz et al. |
| 2006/0069415 A1 | 3/2006 | Cameron et al. |
| 2006/0094951 A1 | 5/2006 | Dean et al. |
| 2006/0095088 A1 | 5/2006 | De Riddler |
| 2006/0155340 A1 | 7/2006 | Schuler et al. |
| 2006/0206169 A1 | 9/2006 | Schuler |
| 2006/0218007 A1 | 9/2006 | Bjorner et al. |
| 2006/0224189 A1 | 10/2006 | Schuler et al. |
| 2006/0235472 A1 | 10/2006 | Goetz et al. |
| 2006/0259079 A1 | 11/2006 | King |
| 2006/0259099 A1 | 11/2006 | Goetz et al. |
| 2007/0000372 A1 | 1/2007 | Rezai et al. |
| 2007/0017749 A1 | 1/2007 | Dold et al. |
| 2007/0027514 A1 | 2/2007 | Gerber |
| 2007/0043268 A1 | 2/2007 | Russell |
| 2007/0049817 A1 | 3/2007 | Preiss et al. |
| 2007/0067003 A1 | 3/2007 | Sanchez et al. |
| 2007/0078498 A1 | 4/2007 | Rezai et al. |
| 2007/0083104 A1 | 4/2007 | Butson et al. |
| 2007/0123953 A1 | 5/2007 | Lee et al. |
| 2007/0129769 A1 | 6/2007 | Bourget et al. |
| 2007/0135855 A1 | 6/2007 | Foshee et al. |
| 2007/0156186 A1 | 7/2007 | Lee et al. |
| 2007/0162086 A1 | 7/2007 | DiLorenzo |
| 2007/0162235 A1 | 7/2007 | Zhan et al. |
| 2007/0168004 A1 | 7/2007 | Walter |
| 2007/0168007 A1 | 7/2007 | Kuzma et al. |
| 2007/0185544 A1 | 8/2007 | Dawant et al. |
| 2007/0191887 A1 | 8/2007 | Schuler et al. |
| 2007/0191912 A1 | 8/2007 | Ficher et al. |
| 2007/0197891 A1 | 8/2007 | Shachar et al. |
| 2007/0203450 A1 | 8/2007 | Berry |
| 2007/0203532 A1 | 8/2007 | Tass et al. |
| 2007/0203537 A1 | 8/2007 | Goetz et al. |
| 2007/0203538 A1 | 8/2007 | Stone et al. |
| 2007/0203539 A1 | 8/2007 | Stone et al. |
| 2007/0203540 A1 | 8/2007 | Goetz et al. |
| 2007/0203541 A1 | 8/2007 | Goetz et al. |
| 2007/0203543 A1 | 8/2007 | Stone et al. |
| 2007/0203544 A1 | 8/2007 | Goetz et al. |
| 2007/0203545 A1 | 8/2007 | Stone et al. |
| 2007/0203546 A1 | 8/2007 | Stone et al. |
| 2007/0213789 A1 | 9/2007 | Nolan et al. |
| 2007/0213790 A1 | 9/2007 | Nolan et al. |

(56) References Cited

U.S. PATENT DOCUMENTS

| | | |
|---|---|---|
| 2007/0244519 A1 | 10/2007 | Keacher et al. |
| 2007/0245318 A1 | 10/2007 | Goetz et al. |
| 2007/0255321 A1 | 11/2007 | Gerber et al. |
| 2007/0255322 A1 | 11/2007 | Gerber et al. |
| 2007/0265664 A1 | 11/2007 | Gerber et al. |
| 2007/0276441 A1 | 11/2007 | Goetz |
| 2007/0282189 A1 | 12/2007 | Dan et al. |
| 2007/0288064 A1 | 12/2007 | Butson et al. |
| 2008/0027514 A1 | 1/2008 | DeMulling et al. |
| 2008/0039895 A1 | 2/2008 | Fowler et al. |
| 2008/0071150 A1 | 3/2008 | Miesel et al. |
| 2008/0081982 A1 | 4/2008 | Simon et al. |
| 2008/0086451 A1 | 4/2008 | Torres et al. |
| 2008/0103533 A1 | 5/2008 | Patel et al. |
| 2008/0114233 A1 | 5/2008 | McIntyre et al. |
| 2008/0114579 A1 | 5/2008 | McIntyre et al. |
| 2008/0123922 A1 | 5/2008 | Gielen et al. |
| 2008/0123923 A1 | 5/2008 | Gieten et al. |
| 2008/0133141 A1 | 6/2008 | Frost |
| 2008/0141217 A1 | 6/2008 | Goetz et al. |
| 2008/0154340 A1 | 6/2008 | Goetz et al. |
| 2008/0154341 A1 | 6/2008 | McIntyre et al. |
| 2008/0163097 A1 | 7/2008 | Goetz et al. |
| 2008/0183256 A1 | 7/2008 | Keacher |
| 2008/0188734 A1 | 8/2008 | Suryanarayanan et al. |
| 2008/0215118 A1 | 9/2008 | Goetz et al. |
| 2008/0227139 A1 | 9/2008 | Deisseroth et al. |
| 2008/0242950 A1 | 10/2008 | Jung et al. |
| 2008/0261165 A1 | 10/2008 | Steingart et al. |
| 2008/0269588 A1 | 10/2008 | Csavoy et al. |
| 2008/0300654 A1 | 12/2008 | Lambert et al. |
| 2008/0300797 A1 | 12/2008 | Tabibiazar et al. |
| 2009/0016491 A1 | 1/2009 | Li |
| 2009/0054950 A1 | 2/2009 | Stephens |
| 2009/0082640 A1 | 3/2009 | Kovach et al. |
| 2009/0082829 A1 | 3/2009 | Panken et al. |
| 2009/0112289 A1 | 4/2009 | Lee et al. |
| 2009/0118635 A1 | 5/2009 | Lujan et al. |
| 2009/0118786 A1 | 5/2009 | Meadows et al. |
| 2009/0149917 A1 | 6/2009 | Whitehurst et al. |
| 2009/0196471 A1 | 8/2009 | Goetz et al. |
| 2009/0196472 A1 | 8/2009 | Goetz et al. |
| 2009/0198306 A1 | 8/2009 | Goetz et al. |
| 2009/0198354 A1 | 8/2009 | Wilson |
| 2009/0204192 A1 | 8/2009 | Carlton et al. |
| 2009/0208073 A1 | 8/2009 | McIntyre et al. |
| 2009/0210208 A1 | 8/2009 | McIntyre et al. |
| 2009/0242399 A1 | 10/2009 | Kamath et al. |
| 2009/0276008 A1 | 11/2009 | Lee et al. |
| 2009/0281595 A1 | 11/2009 | King et al. |
| 2009/0281596 A1 | 11/2009 | King et al. |
| 2009/0287271 A1 | 11/2009 | Blum et al. |
| 2009/0287272 A1 | 11/2009 | Kokones et al. |
| 2009/0287273 A1 | 11/2009 | Carlton et al. |
| 2009/0287467 A1 | 11/2009 | Sparks et al. |
| 2009/0299164 A1 | 12/2009 | Singhal et al. |
| 2009/0299165 A1 | 12/2009 | Singhal et al. |
| 2009/0299380 A1 | 12/2009 | Singhal et al. |
| 2010/0010566 A1 | 1/2010 | Thacker et al. |
| 2010/0010646 A1 | 1/2010 | Drew et al. |
| 2010/0023103 A1 | 1/2010 | Elborno |
| 2010/0023130 A1 | 1/2010 | Henry et al. |
| 2010/0030312 A1 | 2/2010 | Shen |
| 2010/0049276 A1 | 2/2010 | Blum et al. |
| 2010/0049280 A1 | 2/2010 | Goetz |
| 2010/0064249 A1 | 3/2010 | Groetken |
| 2010/0113959 A1 | 5/2010 | Pascual-Leon et al. |
| 2010/0121409 A1 | 5/2010 | Kothandaraman et al. |
| 2010/0135553 A1 | 6/2010 | Joglekar |
| 2010/0137944 A1 | 6/2010 | Zhu |
| 2010/0152604 A1 | 6/2010 | Kuala et al. |
| 2010/0179562 A1 | 7/2010 | Linker et al. |
| 2010/0324410 A1 | 12/2010 | Paek et al. |
| 2010/0331883 A1 | 12/2010 | Schmitz et al. |
| 2011/0040351 A1 | 2/2011 | Buston et al. |
| 2011/0066407 A1 | 3/2011 | Butson et al. |
| 2011/0172737 A1 | 7/2011 | Davis et al. |
| 2011/0184487 A1 | 7/2011 | Alberts et al. |
| 2011/0191275 A1 | 8/2011 | Lujan et al. |
| 2011/0196253 A1 | 8/2011 | McIntyre et al. |
| 2011/0213440 A1 | 9/2011 | Fowler et al. |
| 2011/0306845 A1 | 12/2011 | Osorio |
| 2011/0306846 A1 | 12/2011 | Osorio |
| 2011/0307032 A1 | 12/2011 | Goetz et al. |
| 2012/0027272 A1 | 2/2012 | Akinyemi et al. |
| 2012/0046715 A1 | 2/2012 | Moffitt et al. |
| 2012/0078106 A1 | 3/2012 | Dentinger et al. |
| 2012/0089205 A1 | 4/2012 | Boyden et al. |
| 2012/0116476 A1 | 5/2012 | Kothandaraman |
| 2012/0165898 A1 | 6/2012 | Moffitt |
| 2012/0165901 A1 | 6/2012 | Zhu et al. |
| 2012/0207378 A1 | 8/2012 | Gupta et al. |
| 2012/0226138 A1 | 9/2012 | DeSalles et al. |
| 2012/0229468 A1 | 9/2012 | Lee et al. |
| 2012/0265262 A1 | 10/2012 | Osorio |
| 2012/0265268 A1 | 10/2012 | Blum et al. |
| 2012/0302912 A1 | 11/2012 | Moffitt et al. |
| 2012/0303087 A1 | 11/2012 | Moffitt et al. |
| 2012/0314924 A1 | 12/2012 | Carlton et al. |
| 2012/0316619 A1 | 12/2012 | Goetz et al. |
| 2013/0039550 A1 | 2/2013 | Blum et al. |
| 2013/0060305 A1 | 3/2013 | Bokil |
| 2013/0116748 A1 | 5/2013 | Bokil et al. |
| 2013/0116749 A1 | 5/2013 | Carlton et al. |
| 2013/0116929 A1 | 5/2013 | Carlton et al. |
| 2014/0067018 A1 | 3/2014 | Carcieri et al. |
| 2014/0277284 A1 | 9/2014 | Chen et al. |
| 2015/0080695 A1 | 3/2015 | Rogers et al. |
| 2015/0134031 A1 | 5/2015 | Moffitt et al. |

FOREIGN PATENT DOCUMENTS

| | | |
|---|---|---|
| EP | 1372780 | 1/2004 |
| EP | 1559369 | 8/2005 |
| WO | 97/39797 | 10/1997 |
| WO | 98/48880 | 11/1998 |
| WO | 02/26314 | 4/2002 |
| WO | 02/28473 | 4/2002 |
| WO | 02/065896 | 8/2002 |
| WO | 02/072192 | 9/2002 |
| WO | 03/086185 | 10/2003 |
| WO | 2004/019799 A2 | 3/2004 |
| WO | 2004041080 | 5/2005 |
| WO | 2006017053 | 2/2006 |
| WO | 2006113305 | 10/2006 |
| WO | 2007/097859 | 8/2007 |
| WO | 20071097861 A1 | 8/2007 |
| WO | 2007/100427 | 9/2007 |
| WO | 2007/100428 | 9/2007 |
| WO | 2007/112061 | 10/2007 |
| WO | 2009097224 | 8/2009 |
| WO | 2010/120823 A2 | 10/2010 |
| WO | 2011025865 | 3/2011 |
| WO | 01/90876 | 11/2011 |
| WO | 2011/139779 A1 | 11/2011 |
| WO | 2011/159688 A2 | 12/2011 |
| WO | 2012088482 | 6/2012 |
| WO | 2014/036081 | 3/2014 |

OTHER PUBLICATIONS

Nowinski, W. L., et al., "Statistical analysis of 168 bilateral subthalamic nucleus implantations by means of the probabilistic functional atlas ", Neurosurgery 57(4 Suppl) (Oct. 2005),319-30.

Obeso, J. A , et al., "Deep-brain stimulation of the subthalamic nucleus or the pars interna of the globus palidus in Parkinson's disease.", N Engl J Med , 345{13l. The Deep-Brain Stimulation for Parkinson's Disease Study Group, (Sep. 27, 2001 ),956-63.

Butson et al.. "Current Steering to control the volume of tissue activated during deep brain stimulation," vol. 1, No. 1, Dec. 3, 2007, pp. 7-15.

(56) References Cited

OTHER PUBLICATIONS

Patrick, S. K., et al., "Quantification of the UPDRS rigidity scale", IEEE Transactions on Neural Systems and Rehabilitation Engineering, [see also IEEE Trans. on Rehabilitation Engineering 9(1). (2001),31-41.
Phillips, M. D., et al., "Parkinson disease: pattern of functional MR imaging activation during deep brain stimulation of subthalamic nucleus—initial experience", Radiology 239(1). (Apr. 2006),209-16.
Ericsson, A. et al., "Construction of a patient-specific atlas of the brain: Application to normal aging," Biomedical Imaging: From Nano to Macro, ISBI 2008, 5th IEEE international Symposium, May 14, 2008, pp. 480-483.
Kaikai Shen et al., "Atlas selection strategy using least angle regression multi-atlas segmentation propagation," Biomedical Imaging: From Nano to Macro, 2011, 8th IEEE International Symposium, ISBI 2011, Mar. 30, 2011, pp. 1746-1749.
Liliane Ramus et al., "Assessing selection methods in the cotnext of multi-atlas based segmentation," Biomedical Imaging: From Nano to Macro, 2010, IEEE International Symposium, Apr. 14, 2010, pp. 1321-1324.
Olivier Commowick et al., "Using Frankenstein's Creature Paradigm to Build a Patient Specific Atlas," 2009, Medical Image Computing and Computer-Assisted Intervention, pp. 993-1000.
Lotjonen J.M.P. et al., "Fast and robust multi-atlas segmentation of brain magnetic resonance images," NeuroImage, Academic Press, vol. 49, No. 3, Feb. 1, 2010, pp. 2352-2365.
McIntyre, C. C., et al., "How does deep brain stimulation work? Present understanding and future questions." J Clin Neurophysiol. 21 (1 ). (Jan.-Feb. 2004 ),40-50.
Sanchez Castro et al., "A cross validation study of deep brain stimulation targeting: From experts to Atlas-Based, Segmentation-Based and Automatic Registration Algorithms," IEEE Transactions on Medical Imaging, vol. 25, No. 11, Nov. 1, 2006, pp. 1440-1450.
Plaha, P. , et al., "Stimulation of the caudal zone incerta is superior to stimulation of the subthalamic nucleus in improving contralateral parkinsonism.", Brain 129{Pt 7) (Jul. 2006), 1732-4 7.
Rattay, F, "Analysis of models for external stimulation of axons", IEEE Trans. Biomed. Eng. vol. 33 (1986),974-977.
Rattay, F., "Analysis of the electrical excitation of CNS neurons", IEEE Transactions on Biomedical Engineering 45 (6). (Jun. 1998),766-772.
Rose, T. L., et al., "Electrical stimulation with Pt electrodes. VIII. Electrochemically safe charge injection limits with 0.2 ms pulses [neuronal application]", IEEE Transactions on Biomedical Engineering, 37(11 }, (Nov. 1990), 1118-1120.
Rubinstein, J. T., et al., "Signal coding in cochlear implants: exploiting stochastic effects of electrical stimulation", Ann Otol Rhinol Laryngol Suppl. 191, (Sep. 2003), 14-9.
Schwan, H.P., et al., "The conductivity of living tissues.", Ann NY Acad Sci., 65(6). (AUQ., 1957),1007-13.
Taylor, R. S. et al., "Spinal cord stimulation for chronic back and leg pain and failed back surgery syndrome: a systematic review and analysis of prognostic factors", Spine 30(1 ). (Jan. 1, 2005), 152-60.
Siegel, Ralph M. et al., "Spatiotemporal dynamics of the functional architecture for gain fields in inferior parietal lobule of behaving monkey" Cerebral Cortex, New York, NY. vol. 17, No. 2, Feb. 2007, pp. 378-390 1 i.
Klein, A. et al., "Evaluation of 14 nonlinear deformation algorithms applied to human brain MRI registration," NeuroImage, Academic Press, Orlando, FL, vol. 46, No. 3, Jul. 2009, pp. 786-802.
Geddes, L. A., et al., "The specific resistance of biological material—a compendium of data for the biomedical engineer and physiologist.", Med Biol Ena. 5(3). (May 1967),271-93.
Gimsa, J., et al., "Choosing electrodes for deep brain stimulation experiments-electrochemical considerations.", J Neurosci Methods, 142(2), (Mar. 30, 2005),251-65.
Vidailhet, M. , et al., "Bilateral deep-brain stimulation of the globus pallidus in primary generalized dystonia", N Engl J Med. 352(5) (Feb. 3, 2005),459-67.

Izad, Oliver, "Computationally Efficient Method in Predicating Axonal Excitation," Dissertation for Master Degree, Department of Biomedical Engineering, Case Western Reserve University, May 2009.
Jaccard, Paul, "Elude comparative de la distribution florale dans une portion odes Aples et des Jura," Bulletin de la Societe Vaudoise des Sciences Naturelles (1901), 37:547-579.
Dice, Lee R., "Measures of the Amount of Ecologic Association Between Species," Ecology 26(3) (1945): 297-302. doi: 10.2307/1932409, http://jstor.org/stable/1932409.
Rand, WM., "Objective criteria for the evaluation of clustering methods," Journal of the American Statistical Association (American Statistical Association) 66 (336) (1971 ): 846-850, doi:10.2307/2284239, http://jstor.org/stable/2284239.
Hubert, Lawrence et al., "Comparing partitions," Journal of Classification 2(1) (1985): 193-218, doi: 10.1007/ BF01908075.
Cover, T.M. et al., "Elements of information theory," (1991) John Wiley & Sons, New York, NY.
Meila, Marina, "Comparing Clusterings by the Variation of Information," Learning Theory and Kernel Machines (2003) 173-187.
Viola, P., et al., "Alignment by maximization of mutual information", International Journal of Corn outer Vision 24(2). ( 1997), 137-154
Butson et al. "StimExplorer: Deep Brain Stimulation Parameter Selection Software System," Acta Neurochirugica, Jan. 1, 2007, vol. 97, No. 2, pp. 569-574.
Butson et al. "Role of Electrode Design on the Volume of Tissue Activated During Deep Brain Stimulation," Journal of Neural Engineering, Mar. 1, 2006, vol. 3, No. 1, pp. 1-8.
Volkmann et al., Indroduction to the Programming of Deep Brain Stimulators, Movement Disorders, vol. 17, Suppl. 3, pp. S181-S187 (2002).
Miocinovic et al. "Cicerone: Stereotactic Neurophysiological Recording and Deep Brain Stimulation Electrode Placement Software System," Acta Neurochirurgica Suppl., Jan. 1, 2007, vol. 97, No. 2, pp. 561-567.
Schmidt et al. "Sketching and Composing Wdgets for 3D Manipulation," Eurographics, Apr. 2008, vol. 27, No. 2, pp. 301-310.
Volkmann, J. , et al., "Basic algorithms for the programming of deep brain stimulation in Parkinson's disease", Mov Disord., 21 Suppl 14. (Jun. 2006),S284-9.
Walter, B. L., et al., "Surgical treatment for Parkinson's disease", Lancet Neural. 3(12). (Dec. 2004), 719-28.
Wei, X. F., et al.; "Current density distributions, field distributions and impedance analysis of segmented deep brain stimulation electrodes", J Neural Eng .. 2(4). (Dec. 2005), 139-47.
Zonenshayn, M. , et al., "Location of the active contact within the subthalamic nucleus (STN) in the treatment of idiopathic Parkinson's disease.", Surg Neurol., 62(3) (Sep. 2004),216-25.
Da Silva et al (A primer on diffusion tensor imaging of anatomical substructures. Neurosurg Focus 15(1): p. 1-4, Article 4, 2003.).
Micheli-Tzanakou, E., et al., "Computational intelligence for target assesment in Parkinson's disease", Proceedings of SPIE vol. 4479. Applications and Science of Neural Networks, Fuzzy Systems, and Evolutionary Computation IV,(2001),54-69.
Grill, W. M., "Stimulus waveforms for selective neural stimulation", IEEE Engineering in Medicine and Biology Magazine, 14(4}, (Jul.-Aug. 1995), 375-385.
Miocinovic, S., et al.; "Sensitivity of temporal excitation properties to the neuronal element activated by extracellular stimulation", J Neurosci Methods. 132(1). (Jan, 15, 2004), 91-9.
Hunka, K. et al., Nursing Time to Program and Assess Deep Brain Stimulators in Movement Disorder Patients; J. Neursci Nurs., 37: 204-10 (Aug. 2005).
Moss, J. , et al., "Electron microscopy of tissue adherent to explanted electrodes in dystonia and Parkinson's disease", Brain, 127(Pt 12). (Dec. 2004 ),2755-63.
Montgomery, E. B., et al., "Mechanisms of deep brain stimulation and future technical developments.", Neurol Res. 22(3). (Apr. 2000),259-66.
Merrill, D. R., et al., "Electrical stimulation of excitable tissue: design of efficacious and safe protocols", J Neurosci Methods. 141(2), (Feb. 15, 2005), 171-98.

(56) References Cited

OTHER PUBLICATIONS

Fisekovic et al., "New Controller for Functional Electrical Stimulation Systems", Med. Eng. Phys. 2001; 23:391-399.
Zhang, Y., et al., "Atlas-guided tract reconstruction for automated and comprehensive examination of the white matter anatomy" Neuroimage 52(4) (2010), pp. 1289-1301.
"BioPSE The Biomedical Problem Solving Environment", htt12://www.sci.utah.edu/cibc/software/index.html, MCRR Center for Integrative Biomedical Computing,(2004).
Andrews, R. J., "Neuroprotection trek—the next gerneration: neuromodulation I. Techniques—deep brain stimulation, vagus nerve stimulation, and transcranial magnetic stimulation.", Ann NY Acad Sci. 993. (May 2003), 1-13.
Carnevale, N.T. et al., "The Neuron Book," Cambridge, UK: Cambridge University Press (2006), 480 pages.
Chaturvedi: "Development of Accurate Computational Models for Patient-Specific Deep Brain Stimulation," Thesis or Dissertation, Jan. 2012, 162 pages.
Chaturvedi, A. et al.: "Patient-specific models of deep brain stimulation: Influence of field model complexity on neural activation predictions." Brain Stimulation, Elsevier, Amsterdam, NL, vol. 3, No. 2, Apr. 2, 2010, pp. 65-77.
Frankemolle, et al., "Reversing cognitive-motor impairments in Parkinson's disease patients using a computational modeling approach to deep brain stimulation programming," Brian 133 (2010), pp. 746-761.
McIntyre, C.C., et al., "Modeling the exc tablitity of mammalian nerve fibers: influence of afterpotentials on the recovery cycle," J Neurophysiol, 87(2) (Feb. 2002), pp. 995-1006.
Peterson, et al., "Predicting myelinated axon activation using spatial characteristics of the extracellular field," Journal of Neural Engineering, 8 (2011), 12 pages.
Warman, et al., "Modeling the Effects of Electric Fields on nerver Fibers; Dermination of Excitation Thresholds,"IEEE Transactions on Biomedical Engineering, vol. 39, No. 12 (Dec. 1992), pp. 1244-1254.
Wesselink, et al., "Analysis of Current Density and Related Parameters in Spinal Cord Stimulation," IEEE Transactions on Rehabilitation Engineering, vol. 6. No. 2 Jun. 1998, pp. 200-207.
Andrews, R. J., "Neuroprotection trek—the next generation: neuromodulation II. Applications—epilepsy, nerve regeneration, neurotrophins.", Ann NY Acad Sci. 993 (May 2003), 14-24.
Astrom, M. , et al., "The effect of cystic cavities on deep brain stimulation in the basal ganglia: a simulation-based study", J Neural Eng., 3(2), (Jun. 2006).132-8.
Bazin et al., "Free Software Tools for Atlas-based Volumetric Neuroimage Analysis", Proc. SPIE 5747, Medical Imaging 2005: Image Processing, 1824 May 5, 2005.
Back, C. , et al., "Postoperative Monitoring of the Electrical Properties of Tissue and Electrodes in Deep Brain Stimulation", Neuromodulation, 6(4), (Oct. 2003 )248-253.
Baker, K. B., et al., "Evaluation of specific absorption rate as a dosimeter of MRI-related implant heating", J Magn Reson Imaging., 20(2), (Aug. 2004),315-20.
Brown, J. "Motor Cortex Stimulation," Neurosurgical Focus ( Sep. 15, 2001) 11(3):E5.
Budai et al., "Endogenous Opioid Peptides Acting at m-Opioid Receptors in the Dorsal Horn Contribute to Midbrain Modulation of Spinal Nociceptive Neurons," Journal of Neurophysiology (1998) 79(2): 677-687.
Cesselin, F. "Opioid and anti-opioid peptides," Fundamental and Clinical Pharmacology (1995) 9(5): 409-33 (Abstract only).
Rezai et al., "Deep Brain Stimulation for Chronic Pain" Surgical Management of Pain. Chapter 44 pp. 565-576 (2002).
Xu, MD., Shi-Ang, article entitled "Comparison of Half-Band and Full-Band Electrodes for Intracochlear Electrical Stimulation", Annals of Otology, Rhinology & Laryngology (Annals of Head & Neck Medicine & Surgery), vol. 102 (5) pp. 363-367 May 1993.

Bedard, C. , et al., "Modeling extracellular field potentials and the frequency-filtering properties of extracellular space", Biophys J .. 86(3). (Mar. 2004),1829-42.
Benabid, A. L., et al., "Future prospects of brain stimulation", Neurol Res.;22(3), (Apr. 2000),237-46.
Brummer, S. B., et al., "Electrical Stimulation with Pt Electrodes: II—Estimation of Maximum Surface Redox (Theoretical Non-Gassing) Limits", IEEE Transactions on Biomedical Engineering, vol. BME-24, Issue 5, (Sep. 1977),440-443.
Butson, Christopher R., et al., "Deep Brain Stimulation of the Subthalamic Nucleus: Model-Based Analysis of the Effects of Electrode Capacitance on the Volume of Activation", Proceedings of the 2nd International IEEE EMBS, (Mar. 16-19, 2005),196-197.
McIntyre, Cameron C., et al., "Cellular effects of deep brain stimulation: model-based analysis of activation and inhibition," J Neurophysiol, 91(4) (Apr. 2004), pp. 1457-1469.
Chaturvedi, A., et al., "Subthalamic Nucleus Deep Brain Stimulation: Accurate Axonal Threshold Prediction with Diffusion Tensor Based Electric Field Models", Engineering in Medicine and Biology Society, 2006. EMBS' 06 28th Annual International Conference of the IEEE, IEEE, Piscataway, NJ USA, Aug. 30, 2006.
Butson, Christopher et al., "Predicting the Effects of Deep Brain Stimulation with Diffusion Tensor Based Electric Field Models" Jan. 1, 2001, Medical Image Computing and Computer-Assisted Intervention-Mic CAI 2006 Lecture Notes in Computer Science; LNCS, Springer, Berlin, DE.
Butson, C. R., et al., "Deep brainstimulation interactive visualization system", Society for Neuroscience vol. 898.7 (2005).
Hodaie, M., et al., "Chronic anterior thalamus stimulation for intractable epilepsy," Epilepsia, 43(6) (Jun. 2002), pp. 603-608.
Hoekema R., et al., "Multigrid solution of the potential field in modeling electrical nerve stimulation," Comput Biomed Res., 31(5) (Oct. 1998), pp. 348-362.
Holsheimer, J., et al., "Identification of the target neuronal elements in electrical deep brain stimulation," Eur J Neurosci., 12(12) (Dec. 2000), pp. 4573-4577.
Jezernik, S., et al., "Neural network classification of nerve activity recorded in a mixed nerve," Neurol Res., 23(5) (Jul. 2001), pp. 429-434.
Jones, DK., et al., "Optimal strategies for measuring diffusion in anisotropic systems by magnetic resonance imaging," Magn. Reson. Med., 42(3) (Sep. 1999), pp. 515-525.
Krack. P., et al., "Postoperative management of subthalamic nucleus stimulation for Parkinson's disease," Mov. Disord., vol. 17(suppl 3) (2002), pp. 188-197.
Le Bihan, D., et al., "Diffusion tensor imaging: concepts and applications," J Magn Reson imaging, 13(4) (Apr. 2001), pp. 534-546.
Lee, D. C., et al., "Extracellular electrical stimulation of central neurons: quantitative studies," In: Handbook of neuroprosthetic methods, WE Finn and PG Lopresti (eds) CRC Press (2003), pp. 95-125.
Levy, AL., et al., "An Internet-connected, patient-specific, deformable brain atlas integrated into a surgical navigation system," J Digit Imaging, 10(3 Suppl 1) (Aug. 1997), pp. 231-237.
Liu, Haiying, et al., "Intra-operative MR-guided DBS implantation for treating PD and ET," Proceedings of SPIE vol. 4319, Department of Radiology & Neurosurgery, University of Minnesota, Minneapolis, MN 55455 (2001), pp. 272-276.
Mcintyre, C. C., et al., "Extracellular stimulation of central neurons: influence of stimulus waveform and frequency on neuronal output," J. Neurophysiol., 88(4), (Oct. 2002), pp. 1592-1604.
Mcintyre, C. C., et al., "Microstimulation of spinal motoneurons: a model study," Proceedings of the 19th Annual International Conference of the IEEE Engineering in Medicine and Biology society, vol. 5, (1997), pp. 2032-2034.
Mcintyre, Cameron C., et al., "Model-based Analysis of deep brain stimulation of the thalamus," Proceedings of the Second joint EMBS/BM ES Conference, vol. 3, Annual Fall Meeting of the Biomedical Engineering Society (Cal. No. 02CH37392) UEEEPiscataway, NJ (2002), pp. 2047-2048.
Macintyre, C. C., et al., "Model-based design of stimulus trains for selective microstimulation of targeted neuronal populations," Pro-

(56) References Cited

OTHER PUBLICATIONS ceedings of the 23rd Annual International Conference of the IEEE Engineering in Medicine and Biology Society, vol. 1 (2001), pp. 806-809.

Mcintyre, C. C., et al., Model-based design of stimulus waveforms for selective microstimulation in the central nervous system,, Proceedings of the First Joint |Engineering in Medicine and Biology, 1999. 21st Annual Conf. and the 1999 Annual FallMeeting of the Biomedical Engineering Soc.] BM ES/EMBS Conference, vol. 1 (1999), p. 384.

Mcintyre, Cameron C., et al., "Modeling the excitability of mammalian nerve fibers: influence of afterpotentials on the recovery cycle," J Neurophysiol, 87(2) (Feb. 2002), pp. 995-1006.

Mcintyre, Cameron C., et al., "Selective microstimulation of central nervous system neurons," Annals of biomedical engineering, 28(3) (Mar. 2000), pp. 219-233.

Mcintyre, C. C., et al., "Sensitivity analysis of a model of mammalian neural membrane." Biol Cybern., 79(1) (Jul. 1998), pp. 29-37.

Mcintyre, Cameron C., et al., "Uncovering the mechanism(s) of action of deep brain stimulation: activation, inhibition, or both," Clin Neurophysiol, 115(6) (Jun. 2004), pp, 1239-1248.

Mcintyre, Cameron C., et al., "Uncovering the mechanisms of deep brain stimulation for Parkinson's disease through imaging, neural recording, and neural modeling," Crit Rev Biomed Eng., 30(4-6) (2002), pp. 249-281.

Mouine et al. "Multi-Strategy and Multi-Algorithm Cochlear Prostheses", Biomed. Sci. Instrument, 2000; 36:233-238.

Mcintyre, Cameron C., et al., "Electric Field and Stimulating Influence generated by Deep Brain Stimulation of the Subthalamaic Nucleus," Clinical Neurophysiology, 115(3) (Mar. 2004), pp. 589-595.

Mcintyre, Cameron C., et al., "Electric field generated by deep brain stimulation of the subthalamic nucleus," Biomedical Engineering Society Annual Meeting, Nashville TN (Oct. 2003), 16 pages.

Mcintyre, Cameron C., et al., "Excitation of central nervous system neurons by nonuniform electric fields," Biophys. J., 76(2) (1999), pp. 878-888.

McNeal, DR., et al., "Analysis of a model for excitation of myelinated nerve," IEEE Trans Biomed Eng., vol. 23 (1976), pp. 329-337.

Micheli-Tzanakou, E. , et al., "Computational Intelligence for target assesment in Parkinson's disease," Proceedings of SPIE vol. 4479. Applications and Science of Neural Networks, Fuzzy Systems, and Evolutionary Computation IV (2001 ), pp. 54-69.

Miocinovic, S., et al., "Computational analysis of subthalamic nucleus and lenticular fasciculus activation during therapeutic deep brain stimulation," J Neurophysiol., 96(3) (Sep. 2006), pp. 1569-1580.

Miranda, P. C. et al., "The distribution of currents inducedin the brain by Magnetic Stimulation: a finite element analysis incorporating OT-MRI-derived conductivity data," Proc. Intl. Soc. Mag. Reson. Med. 9 (2001 ), p. 1540.

Miranda, P. C., et al., "The Electric Field Induced in the Brain by Magnetic Stimulation: A 3-D Finite-Element Analysis of the Effect of Tissue Heterogeneity and Anisotropy," IEEE Transactions on Biomedical Engineering, 50(9) (Sep. 2003), pp. 1074-1085.

Moffitt, MA., et al., "Prediction of myelinated nerve fiber stimulation thresholds: limitations of linear models," IEEE Transactions on Biomedical Engineering, 51 (2) (2003), pp. 229-236.

Moro, E, et al., "The impact on Parkinson's disease of electrical parameter settings in STN stimulation," Neurology, 59(5) (Sep. 10, 2002), pp. 706-713.

Nowak, LG., et al., "Axons, but not cell bodies, are activated by electrical stimulation in cortical gray matter. I. Evidence from chronaxie measurements," Exp. Brain Res., 118(4) (Feb. 1998), pp. 477-488.

Nowak, LG., et al., "Axons, but not cell bodies, are activated by electrical stimulation in cortical gray matter. II. Evidence from selective inactivation of cell bodies and axon initial segments," Exp. Brain Red., 118(4) (Feb. 1998) pp. 489-500.

O'Suilleabhain, PE., et al., "Tremor response to polarity, voltage, pulsewidth and frequency of thalamic stimulation," Neurology, 60(5) (Mar. 11, 2003), pp. 786-790.

Pierpaoli, C., et al., "Toward a quantitative assessment of diffusion anisotropy," Magn Reson Med., 36(6) (Dec. 1996), pp. 893-906.

Plonsey, R., et al., "Considerations of quasi-stationarity in electrophysiological systems," Bull Math Biophys. 29(4) (Dec. 1967), pp. 657-664.

Ranck, J B., "Specific impedance of rabbit cerebral cortex," Exp. Neurol., vol. 7 (Feb. 1963), pp. 144-152.

Ranck, J B., et al., "The Specific impedance of the dorsal columns of the cat: an anisotropic medium," Exp. Neurol., 11 (Apr. 1965), pp. 451-463.

Ranck, J B., "Which elements are excited in electrical stimulation of mammalian central nervous system: a review," Brain Res., 98(3) (Nov. 21, 1975), pp. 417-440.

Rattay, F., et al., "A model of the electrically excited human cochlear neuron. I. Contribution of neural substructures to the generation and propagation of spikes," Hear Res., 153(1-2) (Mar. 2001), pp. 43-63.

Rattay, F., "A model of the electrically excited human cochlear neuron. II. Influence of the three-dimensional cochlear structure on neural excitability," Hear Res., 153(1-2) (Mar. 2001), pp. 64-79.

Rattay, F., "Arrival at Functional Electrostimulation by modelling of fiber excitation," Proceedings of the Ninth annual Conference of the IEEE Engineering in Medicine and Biology Society (1987), pp. 1459-1460.

Rattay, F., "The influence of intrinsic noise can preserve the temporal fine structure of speech signals in models of electrically stimulated human cochlear neurones," Journal of Physiology, Scientific Meeting of the Physiological Society, London, England, UK Apr. 19-21, 1999 (Jul. 1999), p. 170P.

Rizzone, M., et al., "Deep brain stimulation of the subthalamic nucleus in Parkinson's disease: effects of variation in stimulation parameters," J. Neural. Neurosurg. Psychiatry., 71(2) (Aug. 2001), pp. 215-219.

Saint-Cyr, J. A. et al., "Localization of clinically effective stimulating electrodes in the human subthalamic nucleus on magnetic resonance imaging," J. Neurosurg., 87(5) (Nov. 2002), pp. 1152-1166.

Sances, A., et al., "In Electroanesthesia: Biomedical and Biophysical Studies," A Sances and SJ Larson, Eds., Academic Press, NY (1975), pp. 114-124.

SI. Jean, P., et al., "Automated atlas integration and interactive three-dimensional visualization tools for planning and guidance in functional neurosurgery," IEEE Transactions on Medical Imaging, 17(5) (1998), pp. 672-680.

Starr, P.A., et al., "Implantation of deep brain stimulators into the subthalamic nucleus: technical approach and magnetic resonance imaging-verified lead locations," J. Neurosurg., 97(2) (Aug. 2002), pp. 370-387.

Sterio, D., et al., "Neurophysiological refinement of subthalamic nucleus targeting," Neurosurgery, 50(1) (Jan. 2002), pp. 58-69.

Struijk, J. J., et al., "Excitation of dorsal root fibers in spinal cord stimulation: a theoretical study," IEEE Transactions on Biomedical Engineering, 40(7) (Jul. 1993), pp. 632-639.

Struijk, J J., et al., "Recruitment of dorsal column fibers in spinal cord stimulation: influence of collateral branching," IEEE Transactions on Biomedical Engineering, 39(9) (Sep. 1992), pp. 903-912.

Tamma, F., et al., "Anatomo-clinical correlation of intraoperative stimulation-induced side-effects during HF-DBS of the subthalamic nucleus," Neurol Sci., vol. 23 (Suppl 2) (2002), pp. 109-110.

Tarler, M., et al., "Comparison between monopolar and tripolar configurations in chronically implanted nerve cuff electrodes," IEEE 17th Annual Conference Engineering in Medicine and Biology Society, vol. 2 (1995), pp. 1093-1109.

Testerman, Roy L., "Coritical response to callosal stimulation: A model for determining safe and efficient stimulus parameters," Annals of Biomedical Engineering, 6(4) (1978), pp. 438-452.

(56) References Cited

OTHER PUBLICATIONS

Tuch, D.S., et al., "Conductivity mapping of biological tissue using diffusion MRI," Ann NY Acad Sci., 888 (Oct. 30, 1999), pp. 314-316.
Tuch, D.S., et al., "Conductivity tensor mapping of the human brain using diffusion tensor MRI," Proc Nall Acad Sci USA, 98(20) (Sep. 25, 2001), pp. 11697-11701.
Veraart, C., et al., "Selective control of muscle activation with a multipolar nerve cuff electrode," IEEE Transactions on Biomedical Engineering, 40(7) (Jul. 1993), pp. 640-653.
Vercueil, L., et al., "Deep brain stimulation in the treatment of severe dystonia," J. Neurol., 248(8) (Aug. 2001 ), pp. 695-700.
Vilalte, "Circuit Design of the Power-on-Reset," Apr. 2000, pp. 1-25.
Vitek, J. L., "Mechanisms of deep brain stimulation: excitation or inhibition," Mov. Disord., vol. 17 (Suppl. 3) (2002), pp. 69-72.
Voges, J., et el. "Bilateral high-frequency stimulation in the subthalamic nucleus for the treatment of Parkinson disease: correlation of therapeutic effect with anatomical electrode position," J. Neurosurg., 96(2) (Feb. 2002), pp. 269-279.
Wakana, S., et al., "Fiber tract-based atlas of human white matter anatomy," Radiology, 230(1) (Jan. 2004), pp. 77-87.
Alexander, DC., et al., "Spatial transformations of diffusion tensor magnetic resonance images," IEEE Transactions on Medical Imaging, 20 (11), (2001), pp. 1131-1139.
Wu, Y. R., et al., "Does Stimulation of the GPi control dyskinesia by activating inhibitory axons?," Mov. Disord., vol. 16 (2001), pp. 208-216.
Yelnik, J., et al., "Localization of stimulating electrodes in patients with Parkinson disease by using a three-dimensional atlas-magnetic resonance imaging coregistration method," J Neurosurg., 99(1) (Jul. 2003), pp. 89-99.
Yianni, John, et al., "Globus pallidus internus deep brain stimulation for dystoric conditions: a prospective audit," Mov. Disord., vol. 18 (2003), pp. 436-442.
Zonenshayn, M., et al., "Comparison of anatomic and neurophysiological methods for subthalamic nucleus targeting," Neurosurgery, 47(2) (Aug. 2000), pp. 282-294.
Voghell et al., "Programmable Current Source Dedicated to Implantable Microstimulators"ICM '98 Proceedings of the Tenth International Conference. pp. 67-70.
Butson, Christopher R., et al., "Patient-specific analysis of the volume of tissue activated during deep brain stimulation", NeuroImage. vol. 34. (2007),661-670.
Adler, DE., et al., "The tentorial notch: anatomical variation, morphometric analysis, and classification in 100 human autopsy cases," J. Neurosurg., 96(6), (Jun. 2002), pp. 1103-1112.
Jones et al., "An Advanced Demultiplexing System for Physiological Stimulation", IEEE Transactions on Biomedical Engineering, vol. 44 No. 12 Dec. 1997, pp. 1210-1220.
Alo, K. M., et al., "New trends in neuromodulation for the management of neuropathic pain," Neurosurgery, 50(4), (Apr. 2002), pp. 690-703, discussion pp. 703-704.
Ashby, P., et al., "Neurophysiological effects of stimulation through electrodes in the human subthalamic nucleus," Brain, 122 (PI 10), (Oct. 1999), pp. 1919-1931.
Baker, K. B., et al., "Subthalamic nucleus deep brain stimulus evoked potentials: Physiological and therapeutic implications," Movement Disorders, 17(5), (Sep./Oct. 2002), pp. 969-983.
Bammer, R, et al., "Diffusion tensor imaging using single-shot SENSE-EPI", Magn Reson Med., 48(1 ), (Jul. 2002), pp. 128-136.
Basser, P J., et al., "MR diffusion tensor spectroscopy and imaging," Biophys J., 66(1 ), (Jan. 1994), pp. 259-267.
Basser, P J., et al., "New currents in electrical stimulation of excitable tissues," Annu Rev Biomed Eng., 2, (2000), pp. 377-397.
Benabid, AL., et al., "Chronic electrical stimulation of the ventralis intermedius nucleus of the thalamus as a treatment of movement disorders," J. Neurosurg., 84(2), (Feb. 1996), pp. 203-214.

Benabid. AL., et al., "Combined (Ihalamotoy and stimulation) stereotactic surgery of the VIM thalamic nucleus for bilateral Parkinson disease," Appl Neurophysiol, vol. 50, (1987), pp. 344-346.
Benabid, A L., et al., "Long-term suppression of tremor by chronic stimulation of the ventral intermediate thalamic nucleus," Lancet, 337 (8738), (Feb. 16, 1991 ), pp. 403-406.
Butson, C. R., et al., "Predicting the effects of deep brain stimulation with diffusion tensor based electric field models." Medical Image Computing and Computer-Assisted Intervention—Mic Cai 2006, Lecture Notes in Computer Science (LNCS), vol. 4191, pp. 429-437, LNCS, Springer, Berlin, DE.
Christensen, Gary E., et al., "Volumetric transformation of brain anatomy," IEEE Transactions on Medical Imaging, 16(6), (Dec. 1997), pp. 864-877.
Cooper, S , et al., "Differential effects of thalamic stimulation parameters on tremor and paresthesias in essential tremor," Movement Disorders, 17(Supp. 5), (2002), p. S193.
Coubes, P, et al., "Treatment of DYT1-generalised dystonia by stimulation of the internal globus pallidus," (9222), (Jun. 24, 2000), pp. 2220-2221.
Dasilva, A.F. M., et al., "A Primer Diffusion Tensor Imaging of Anatomical Substructures," Neurosurg. Focus; 15(1) (Jul 2003), pp. 1-4.
Dawant, B. M., et al., "Compuerized atlas-guided positioning of deep brain stimulators: a feasibility study," Biomedical Image registration, Second International Workshop, WBIR 2003, Revised Papers (Lecture notes in Comput. Sci. vol. (2717), Springer-Verlag Berlin, Germany(2003), pp. 142-150.
Finnis, K. W., et al., "3-D functional atalas of subcortical structures for image guided stereotactic neurosurgery," Neuroimage, vol. 9, No. 6, Iss. 2 (1999), p. S206.
Finnis, K. W., et al., "3D Functional Database of Subcorticol Structures for Surgical Guidance in Image Guided Stereotactic Neurosurgery," Medical Image Computing and Computer-Assisted Intervention—MICCAI'99, Second International Conference.Cambridge, UK, Sep. 19-22, 1999, Proceedings (1999), pp. 758-767.
Finnis, K. W., et al., "A 3-Dimensional Database of Deep Brain Functional Anatomy, and Its Application to Image-Guided Neurosurgery," Proceedings of the Third International Conference on Medical Image Computing and Computer-Assisted Intervention Lecture Notes in Computer Science; vol. 1935 (2000), pp. 1-8.
Finnis, K. W., et al., "A functional database for guidance of surgical and therapeutic procedures in the deep brain," Proceedings of the 22nd Annual International Conference of the IEEE Engineering in Medicine and Biology Society, vol. 3 (2000), pp. 1787-1789.
Finnis, K. W., et al., "Application of a Population Based Electrophysiological Database to the Planning and Guidance Deep Brain Stereotactic Neurosurgery," Proceedings of the 5th International Conference on Medical Image Computing and Computer-Assisted Intervention—Part 11, Lecture Notes in Computer Science; vol. 2489 (2002), pp. 69-76.
Finnis, K. W., et al., "Subcortical physiology deformed into a patient-specific brain atlas for image-guided stereotaxy," Proceedings of SPIE—vol. 4681 Medical Imaging 2002: Visualization, Image-Guided Procedures, and Display (May 12002), pp. 184-195.
Finnis, Krik W., et al., "Three-Dimensional Database of Subcortical Electrophysiology for Image-Guided Stereotatic Functional Neurosurgery," IEEE Transactions on Medical Imaging, 22(1) (Jan. 2003), pp. 93-104.
Gabriels, L , et al., "Deep brain stimulation for treatment-refractory obsessive-compulsive disorder: psychopathological and neuropsychological outcome in three cases," Acta Psychiatr Scand., 107(4) (2003), pp. 275-282.
Gabriels, LA., et al., "Long-term electrical capsular stimulation in patients with obsessive-compulsive disorder," Neurosurgery, 52(6) (Jun. 2003), pp. 1263-1276.
Goodall, E. V., et al., "Modeling study of activation and propagation delays during stimulation of peripheral nerve fibers with a tripolar cuff electrode," IEEE Transactions on Rehabilitation Engineering, [see also IEEE Trans. on Neural Systems and Rehabilitation], 3(3) (Sep. 1995), pp. 272-282.

(56) References Cited

OTHER PUBLICATIONS

Goodall, E. V., et al., "Position-selective activation of peripheral nerve fibers with a cuff electrode," IEEE Transactions on Biomedical Engineering, 43(8) (Aug. 1996), pp. 851-856.
Goodall, E. V., "Simulation of activation and propagation delay during tripolar neural stimulation," Proceedings of the 15th Annual International Conference of the IEEE Engineering in Medicine and Biology Society (1993), pp. 1203-1204.
Grill, WM., "Modeling the effects of electric fields on nerve fibers: influence of tissue electrical properties," IEEE Transactions on Biomedical Engineering, 46(8) (1999), pp. 918-928.
Grill, W. M., et al., "Neural and connective tissue response to long-term implantation of multiple contact nerve cuff electrodes," J Biomed Mater Res., 50(2) (May 2000), pp. 215-226.
Grill, W. M., "Neural modeling in neuromuscular and rehabilitation research," Proceedings of the 23rd Annual International Conference of the IEEE Engineering in Medicine and Biology Society, vol. 4 (2001 ), pp. 4065-4068.
Grill, W. M., et al., "Non-invasive measurement of the input-output properties of peripheral nerve stimulating electrodes," Journal of Neuroscience Methods, 65(1) (Mar. 1996), pp. 43-50.
Grill, W. M., et al., "Quantification of recruitment properties of multiple contact cuff electrodes," IEEE Transactions on Rehabilitation Engineering, [see also IEEE Trans. on Neural Systems and Rehabilitation]. 4(2) (Jun. 1996), pp. 49-62.
Grill, W. M., "Spatially selective activation of peripheral nerve for neuroprosthetic applications," Ph.D. Case Western Reserve University, (1995), pp. 245 pages.
Grill, W. M., "Stability of the input-output properties of chronically implanted multiple contact nerve cuff stimulation electrods," IEEE Transactions on Rehabilitation Engineering [see also IEEE Trans. on Neural Systems and Rehabilitation] (1998), pp. 364-373.
Grill, W. M., "Stimulus waveforms for selective neural stimulation," IEEE Engineering in Medicine and Biology Magazine, 14(4) (Jul.-Aug. 1995), pp. 375-385.
Grill, W. M., et al., "Temporal stability of nerve cuff electrode recruitment properties," IEEE 17th Annual Conference Engineering in Medicine and Biology Society, vol. 2 (1995), pp. 1089-1090.
Gross, RE., et al., "Advances in neurostimulation for movement disorders," Neurol Res., 22(3) (Apr. 2000), pp. 247-258.
Guridi et al., "The subthalamic nucleus, hemiballismus and Parkinson's disease: reappraisal of a neurological dogma," Brain, vol. 124, 2001, pp. 5-19.
Haberler, C, et al., "No tissue damage by chronic deep brain stimulation in Parkinson's disease," Ann Neurol., 48(3)(Sep. 2000), pp. 372-376.
Hamel, W, et al., "Deep brain stimulation of the subthalamic nucleus in Parkinson's disease: evaluation of active electrode contacts," J Neurol Neurosurg Psychiatry, 74(8) (Aug. 2003), pp. 1036-1046.
Hanekom, "Modelling encapsulation tissue around cochlear implant electrodes," Med. Biol. Eng. Comput. vol. 43 (2005), pp. 47-55.
Haueisen, J , et al., "The influence of brain tissue anisotropy on human EEG and MEG," Neuroimage, 15(1) (Jan. 2002), pp. 159-166.
D'Haese et al. Medical Image Computing and Computer-Assisted Intervention—MICCAI 2005 Lecture Notes in Computer Science, 2005, vol. 3750, 2005, 427-434.
Rohde et al. IEEE Transactions on Medical Imaging, vol. 22 No. 11, 2003 p. 1470-1479.
Dawant et al., Biomedical Image Registration. Lecture Notes in Computer Science, 2003, vol. 2717, 2003, 142-150.
Miocinovic et al., "Stereotactiv Neurosurgical Planning, Recording, and Visualization for Deep Brain Stimulation in Non-Human Primates", Journal of Neurscience Methods, 162:32-41, Apr. 5, 2007, XP022021469.
Gemmar et al., "Advanced Methods for Target Navigation Using Microelectrode Recordings in Stereotactic Neurosurgery for Deep Brain Stimulation", 21st IEEE International Symposium on Computer-Based Medical Systems, Jun. 17, 2008, pp. 99-104, XP031284774.

Acar et al., "Safety Anterior Commissure-Posterior Commissure-Based Target Calculation of the Subthalamic Nucleus in Functional Stereotactic Procedures", Stereotactic Funct. Neurosura., 85:287-291, Aug. 2007.
Andrade-Souza, "Comparison of Three Methods of Targeting the Subthalamic Nucleus for Chronic Stimulation in Parkinson's Disease", Neurosurgery, 56:360-368, Apr. 2005.
Anheim et al., "Improvement in Parkinson Disease by Subthalamic Nucleus Stimulation Based Electrode Placement", Arch Neural., 65:612-616, May 2008.
Butson et al.. "Tissue and Electrode Capacitance Reduce Neural Activation Volumes During Deep Brain Stimulation", Clinical Neurophysiology, 116:2490-2500, Oct. 2005.
Butson et al., "Sources and Effects of Electrode Impedance During Deep Brain Stimulation", Clinical Neurophysiology, 117:44 7-454, Dec. 2005.
D'Haese et al., "Computer-Aided Placement of Deep Brain Stimulators: From Planning to Intraoperative Guidance", IEEE Transaction on Medical Imaging, 24:1469-1478, Nov. 2005.
Gross et al., "Electrophysiological Mapping for the Implantation of Deep Brain Stimulators for Parkinson's Disease and Tremor", Movement Disorders, 21 :S259-S283, Jun. 2006.
Halpern et al., "Brain Shift During Deep Brain Stimulation Surgery for Parkinson's Disease", Stereotact Funct. Neurosurg., 86:37-43, published online Sep. 2007.
Herzog et al., "Most Effective Stimulation Site in Subthalamic Deep Brain Stimulation for Parkinson's Disease", Movement Disorders, 19:1050-1099, published on line Mar. 2004.
Jeon et al., A Feasibility Study of Optical Coherence Tomography for Guiding Deep Brain Probes, Journal of Neuroscience Methods, 154:96-101, Jun. 2006.
Khan et al., "Assessment of Brain Shift Related to Deep Brain Stimulation Surgery", Sterreotact Funct. Neurosurg., 86:44-53, published online Sep. 2007.
Koop et al., "Improvement in a Quantitative Measure of Bradykinesia After Microelectrode Recording in Patients with Parkinson's Disease During Deep Brain Stimulation Surgery", Movement Disorders, 21 :673-678, published on line Jan. 2006.
Lemaire et al., "Brain Mapping in Stereotactic Surgery: A Brief Overview from the Probabilistic Targeting to the Patient-Based Anatomic Mapping", NeuroImage, 37:S109-S115, available online Jun. 2007.
Machado et al., "Deep Brain Stimulation for Parkinson's Disease: Surgical Technique and Perioperative Management", Movement Disorders, 21 :S247-5258, Jun. 2006.
Maks et al., "Deep Brain Stimulation Activation Volumes and Their Association with Neurophysiological Mapping and Therapeutic Outcomes", Downloaded from jnnp.bmj.com, pp. 1-21, published online Apr. 2008.
Moran et al., "Real-Time Refinment of Subthalamic Nucleous Targeting Using Bayesian Decision—Making on the Root Mean Square Measure", Movement Disorders, 21: 1425-1431, published online Jun. 2006.
Sakamoto et al., "Homogeneous Fluorescence Assays for RNA Diagnosis by Pyrene-Conjugated 2'-0-Methyloligoribonucleotides", Nucleosides, Nucleotides, and Nucleric Acids, 26:1659-1664, on line publication Oct. 2007.
Winkler et al., The First Evaluation of Brain Shift During Functional Neurosurgery by Deformation Field Analysis, J. Neural. Neurosurg. Psychiatry, 76:1161-1163, Aug. 2005.
Yelnik et al., "A Three-Dimensional, Histological and Deformable Atlas of the Human Basal J Ganglia. I. Atlas Construction Based on Immunohistochemical and MRI Data", NeuroImage, 34:618,-638,Jan. 2007.
Ward, H. E., et al., "Update on deep brain stimulation for neuropsychiatric disorders," Neurobiol Dis 38 (3) (2010), pp. 346-353.
Alberts et al. "Bilateral subthalamic stimulation impairs cognitive-motor performance in Parkinson's disease patients." Brain (2008), 131, 3348-3360, Abstract.
Butson, Christopher R., et al., "Sources and effects of electrode impedance during deep brain stimulation", Clinical Neurophysiology. vol. 117.(2006),447-454.

(56) References Cited

OTHER PUBLICATIONS

An, et al., "Prefronlal cortical projections to longitudinal columns in the midbrain periaqueductal gray in macaque monkeys," J Comp Neural 401 (4) (1998), pp. 455-479.

Bulson, C. R., et al., "Tissue and electrode capacitance reduce neural activation volumes during deep brain stimulation," Clinical Neurophysiology, vol. 116 (2005), pp. 2490-2500.

Carmichael, S. T., et al., "Connectional networks within the orbital and medial prefronlal cortex of macaque monkeys," J Comp Neural 371 (2) (1996), pp. 179-207.

Croxson, et al., "Quantitative investigation of connections of the prefrontal cortex in the human and macaque using probabilistic diffusion tractography," J Neurosci 25 (39) (2005), pp. 8854-8866.

Frankemolle, et al., "Reversing cognitive-motor impairments in Parkinson's disease patients using a computational modelling approach to deep brain stimulation programming," Brain 133 (2010), pp. 746-761.

Freedman, et al., "Subcortical projections of area 25 (subgenual cortex) of the macaque monkey," J Comp Neural 421 (2) (2000), pp. 172-188.

Giacobbe, et al., "Treatment resistant depression as a failure of brain homeostatic mechanisms: implications for deep brain stimulation," Exp Neural 219 (1) (2009), pp. 44-52.

Goodman, et al., "Deep brain stimulation for intractable obsessive compulsive disorder: pilot study using a blinded, staggered-onset design," Biol Psychiatry 67 (6) (2010), pp. 535-542.

Greenberg, et al., "Deep brain stimulation of the ventral internal capsule/ventral striatum for obsessive-compulsive disorder: worldwide experience," Mol Psychiatry 15 (1) (2010), pp. 64-79.

Greenberg, et al., "Three-year outcomes in deep brain stimulation for highly resistant obsessive-compulsive disorder," Neuropsychopharmacology 31 (11) (2006), pp. 2384-2393.

Gutman, et al., "A tractography analysis of two deep brain stimulation white matter targets for depression," Biol Psychiatry 65 (4) (2009), pp. 276-282.

Haber, et al., "Reward-related cortical inputs define a large striatal region in primates that interface with associative cortical connections, providing a substrate for incentive-based learning," J Neurosci 26 (32) (2006), pp. 8368-8376.

Haber, et al., "Cognitive and limbic circuits that are affected by deep brain stimulation," Front Biosci 14 (2009), pp. 1823-1834.

Hines, M. L., et al., "The NEURON simulation environment," Neural Comput., 9(6) (Aug. 15, 1997), pp. 1179-1209.

Hua, et al., "Tract probability maps in stereotaxic spaces: analyses of white matter anatomy and tract-specific quantification," Neuroimage 39 (1) (2008). pp. 336-347.

Johansen-Berg, et al., "Anatomical connectivity of the subgenual cingulate region targeted with deep brain stimulation for treatment-resistant depression," Cereb Cortex 18 (6) (2008), pp. 1374-1383.

Kopell, et al., "Deep brain stimulation for psychiatric disorders," J Clin Neurophysiol 21 (1) (2004), pp. 51-67.

Lozano, et al., "Subcallosal cingulate gyrus deep brain stimulation for treatment-resistant depression," 64 (6) (2008), pp. 461-467.

Lujan, et al., "Tracking the mechanisms of deep brain stimulation for neuropsychiatric disorders," Front Biosci 13 7 (2008), pp. 5892-5904.

Lujan, J.L. et al., "Automated 3-Dimensional Brain Atlas Fitting to Microelectrode Recordings from Deep Brain Stimulation Surgeries," Stereotact. Funel. Neurosurg. 87(2009), pp. 229-240.

Machado. et al., "Functional topography of the ventral striatum and anterior limb of the internal capsule determined by electrical stimulation of awake patients," Clin Neurophysiol 120 (11) (2009), pp. 1941-1948.

Malone, et al., "Deep brain stimulation of the ventral capsule/ventral striatum for treatment-resistant depression," Biol Psychiatry 65 (4) (2009), pp. 267-275.

Mayberg, H. S., et al., "Deep brain stimulation for treatment-resistant depression," Neuron, 45(5) (Mar. 3, 2005), pp. 651-660.

Mayberg, H. S., et al., "Limbic-cortical dysregulation: a proposed model of depression," J Neuropsychiatry Clin Neurosci. 9 (3) (1997), pp. 471-481.

McIntyre,C. C., et al., "Network perspectives on the mechanisms of deep brain stimulation," Neurobiol Dis 38 (3) (2010), pp. 329-337.

Miocinovic, S., et al., "Experimental and theoretical characterization of the voltage distribution generated by deep brain stimulation," Exp Neurol 216 (i) (2009), pp. 166-176.

Nuttin, et al., "Electrical stimulation in anterior limbs of internal capsules in patients with obsessive-compulsive disorder," Lancet 354 (9189) (1999), p. 1526.

Saxena, et al., "Cerebral glucose metabolism in obsessive-compulsive hoarding," Am J Psychiatry. 161 (6) (2004), pp. 1038-1048.

Viola, et al., "Importance-driven focus of attention," IEEE Trans Vis Comput Graph 12 (5), pp. 933-940.

Wakana, S., et al., "Reproducibility of quantitative tractography methods applied to cerebral white matter," Neuroimage 36 (3) (2007), pp. 630-644.

Mayr et al., "Basic Design and Construction of the Vienna FES Implants: Existing Solutions and Prospects for New Generations of Implants", Medical Engineering & Physics, 2001; 23:53-60.

McIntyre, Cameron , et al., "Finite element analysis of the current-density and electric field generated by metal microelectrodes", Ann Biomed Eng . 29(3), (2001 ),227-235.

Foster, K. R., et al., "Dielectric properties of tissues and biological materials, a critical review.", Grit Rev Biomed Ena. 17(1 ). {1989),25-104.

Limousin, P., et al., "Electrical stimulation of the subthalamic nucleus in advanced Parkinson's disease", N Engl J Med .. 339(16), (Oct. 15, 1998), 1105-11.

Kitagawa, M., et al., "Two-year follow-up of chronic stimulation of the posterior subthalamic white matter for tremor-dominant Parkinson's disease.", Neurosurgery. 56(2). (Feb. 2005),281-9.

Johnson, M. D., et al., "Repeated voltage biasing improves unit recordings by reducing resistive tissue impedances", IEEE Transactions on Neural Systems and Rehabilitation Engineering, [see also IEEE Trans. on Rehabilitation Engineering (2005), 160-165.

Holsheimer, J. , et al., "Chronaxie calculated from current-duration and voltage-duration data", J Neurosci Methods. 97(1). (Apr. 1, 2000),45-50.

Hines, M. L., et al., "The NEURON simulation environment", Neural Comput. 9(6). (Aug. 15, 1997), 1179-209.

Herzog, J., et al., "Most effective stimulation site in subthalamic deep brain stimulation for Parkinson's disease", Mov Disord. 19(9). (Sep. 2004),1050-4.

Hershey, T., et al., "Cortical and subcortical blood flow effects of subthalamic nucleus stimulation in PD.", Neurology 61(6). (Sep. 23, 2003),816-21.

Hemm, S. , et al., "Evolution of Brain Impedance in Dystonic Patients Treated by GPi Electrical Stimulation", Neuromodulation 7(2) (Apr. 2004),67-75.

Hemm, S., et al., "Deep brain stimulation in movement disorders: stereotactic coregistration of two-dimensional electrical field modeling and magnetic resonance imaging.", J Neurosurg. 103(6): (Dec. 2005),949-55.

Haueisen, J. et al., "The influence of brain tissue anisotropy on human EEG and MEG", Neuroimage 15(1) (Jan. 2002),159-166.

Haslinger, B., et al., "Frequency-correlated decreases of motor cortex activity associated with subthalamic nucleus stimulation in Parkinson's disease.", Neuroimage 28(3). (Nov. 15, 2005),598-606.

Hashimoto, T. , et al., "Stimulation of the subthalamic nucleus changes the firing pattern of pallidal neurons", J Neurosci. 23(5). (Mar, 1, 2003),1916-23.

Hardman, C. D., et al., "Comparison of the basal ganglia in rats, marmosets, macaques, baboons, and humans: volume and neuronal number for the output, internal relay, and striatal modulating nuclei", J Comp Neurol., 445(3). (Apr. 8, 2002),238-55.

McNaughtan et al., "Electrochemical Issues in Impedance Tomography", 1st World Congress on Industrial Process Tomography, Buxton, Greater Manchester, Apr, 14-17, 1999.

Grill, WM., et al., "Electrical properties of implant encapsulation tissue", Ann Biomed Eng. vol. 22. (1994),23-33.

(56) References Cited

OTHER PUBLICATIONS

Grill, W. M., et al., "Deep brain stimulation creates an informational lesion of the stimulated nucleus", Neuroreport 15l7t (May 19, 2004), 1137-40.
Partial international Search Report for PCT Application No. PCT/US2016/033969 dated Aug. 10, 2016.
Thomas E. Nichols et al, "Nonparametric Permutation Tests for Functional Neuroimaging: A Primer with Examples," Human Brain Mapping, vol. 15, Jan. 1, 2002 (Jan. 1, 2002), pp. 1-25.

\* cited by examiner

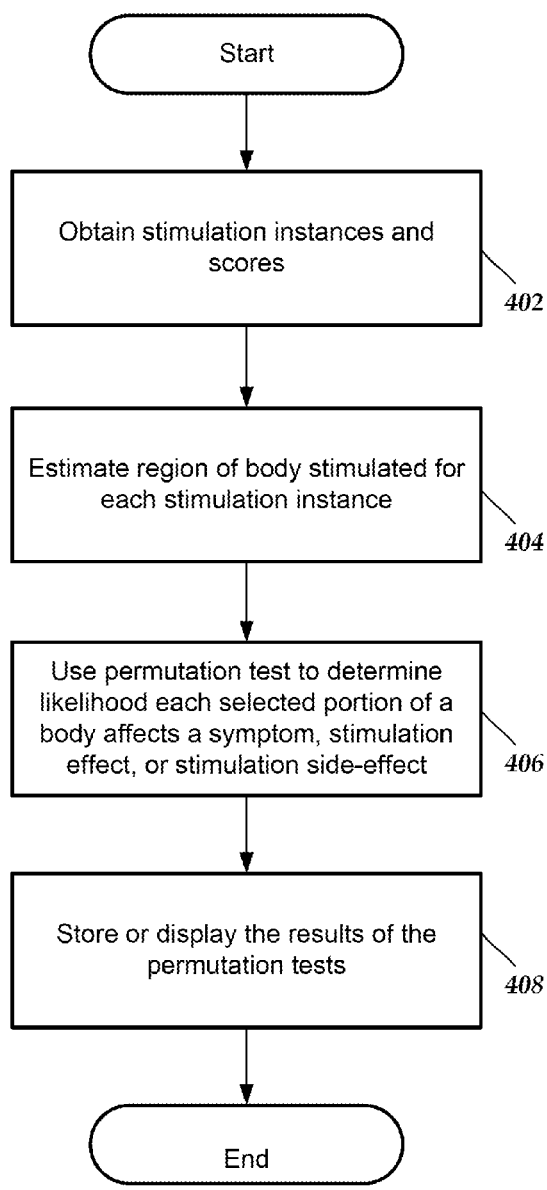
Fig. 4
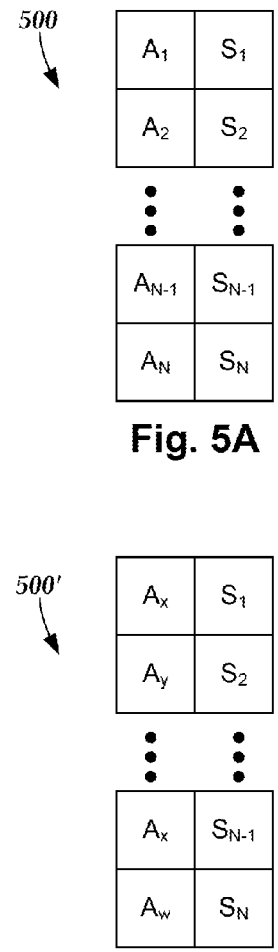
Fig. 5A
Fig. 5B
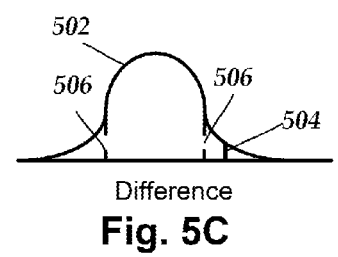
Difference
Fig. 5C

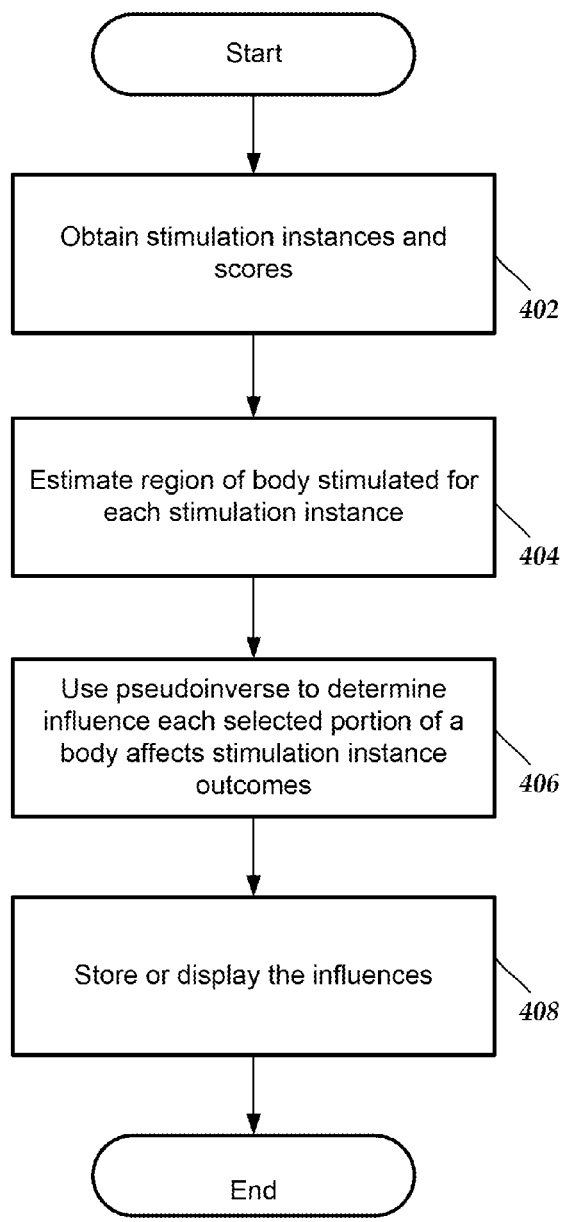
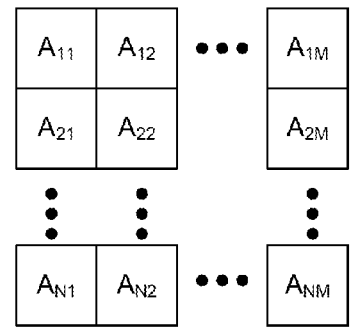
Fig. 7A
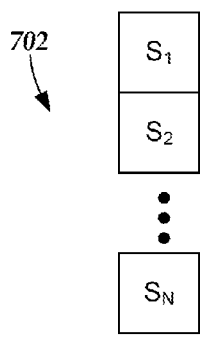
Fig. 7B
Fig. 6

SYSTEMS AND METHODS FOR ANALYZING ELECTRICAL STIMULATION AND SELECTING OR MANIPULATING VOLUMES OF ACTIVATION

CROSS-REFERENCE TO RELATED APPLICATIONS

This application claims the benefit under 35 U.S.C. § 119(e) of U.S. Provisional Patent Application Ser. No. 62/166,569, filed May 26, 2015, which is incorporated herein by reference.

FIELD

The present invention is directed to the area of implantable electrical stimulation systems and methods of making and using the systems. The present invention is also directed to systems for determining regions of the body for stimulation or for selecting or manipulating volumes of activation, as well as methods of making and using the systems.

BACKGROUND

Implantable electrical stimulation systems have proven therapeutic in a variety of diseases and disorders. For example, spinal cord stimulation systems have been used as a therapeutic modality for the treatment of chronic pain syndromes. Peripheral nerve stimulation has been used to treat chronic pain syndrome and incontinence, with a number of other applications under investigation. Functional electrical stimulation systems have been applied to restore some functionality to paralyzed extremities in spinal cord injury patients. Stimulation of the brain, such as deep brain stimulation, can be used to treat a variety of diseases or disorders.

Stimulators have been developed to provide therapy for a variety of treatments. A stimulator can include a control module (with a pulse generator), one or more leads, and an array of stimulator electrodes on each lead. The stimulator electrodes are in contact with or near the nerves, muscles, or other tissue to be stimulated. The pulse generator in the control module generates electrical pulses that are delivered by the electrodes to body tissue.

BRIEF SUMMARY

One embodiment is a system for identifying portions of a body in which electrical stimulation of that portion of the body to treat a condition or disorder affects at least one of at least one symptom of the condition or disorder, stimulation effect, or side effect. The system includes a computer processor configured and arranged to perform the following acts: obtaining, for each of a plurality of stimulation instances, an estimation of a region of the body stimulated during the stimulation instance and a score for each of at least one symptom of the condition or disorder, stimulation effect, or stimulation side effect; determining, for each of a plurality of portions of the body using the scores and the estimates in a permutation test, a likelihood that stimulation of that portion of the body affects at least one symptom of the condition or disorder, stimulation effect, or stimulation side effect; and storing or displaying the determined likelihoods to identify which portions of the body, when electrically stimulated, affect the at least one of the at least one symptom of the condition or disorder, stimulation effect, or stimulation side effect.

Another embodiment is a non-transitory computer-readable medium having processor-executable instructions for identifying portions of a body in which electrical stimulation of that portion of the body to treat a condition or disorder affects at least one of at least one symptom of the condition or disorder, stimulation effect, or side effect, the processor-executable instructions when installed onto a device enable the device to perform actions, including: obtaining, for each of a plurality of stimulation instances, an estimation of a region of the body stimulated during the stimulation instance and a score for each of at least one symptom of the condition or disorder, stimulation effect, or stimulation side effect; determining, for each of a plurality of portions of the body using the scores and the estimates in a permutation test, a likelihood that stimulation of that portion of the body affects at least one symptom of the condition or disorder, stimulation effect, or stimulation side effect; and storing or displaying the determined likelihoods to identify which portions of the body, when electrically stimulated, affect the at least one of the at least one symptom of the condition or disorder, stimulation effect, or stimulation side effect.

Yet another embodiment is a method for identifying portions of a body in which electrical stimulation of that portion of the body to treat a condition or disorder affects at least one of at least one symptom of the condition or disorder, stimulation effect, or side effect. The method includes obtaining, for each of a plurality of stimulation instances, an estimation of a region of the body stimulated during the stimulation instance and a score for each of at least one symptom of the condition or disorder, stimulation effect, or stimulation side effect; determining, for each of a plurality of portions of the body using the scores and the estimates in a permutation test, a likelihood that stimulation of that portion of the body affects at least one symptom of the condition or disorder, stimulation effect, or stimulation side effect; and storing or displaying the determined likelihoods to identify which portions of the body, when electrically stimulated, affect the at least one of the at least one symptom of the condition or disorder, stimulation effect, or stimulation side effect.

In at least some embodiments of the system, non-transitory computer-readable medium, or method described above, further including obtaining the plurality of stimulation instances and, for each stimulation instance, a set of stimulation parameters. In at least some embodiments of the system, non-transitory computer-readable medium, or method described above, obtaining an estimation of a region of the body stimulated during the stimulation instance includes estimating the region of the body stimulation during the stimulation instance based on stimulation parameters used during the stimulation instance.

In at least some embodiments of the system, non-transitory computer-readable medium, or method described above, determining a likelihood includes forming a matrix for a selected portion of the body and for a selected symptom of the condition or disorder, stimulation effect, or stimulation side effect, the matrix including a plurality of rows and columns, where one of the columns or rows corresponds to each stimulation instance, where, for each of a plurality of the stimulation instances, a first entry in a column or row indicates whether the selected portion of the body is stimulated in that stimulation instance and a second entry in the column or row corresponds to the score for the selected symptom of the condition or disorder, stimulation effect, or side effect for that stimulation instance. In at least some embodiments of the system, non-transitory computer-readable medium, or method described above, determining a likelihood further includes determining a likelihood that a null hypothesis is invalid, where the null hypothesis is that the selected portion of the body does not influence the scores for the selected symptom of the condition or disorder, stimulation effect, or side effect. In at least some embodiments of the system, non-transitory computer-readable medium, or method described above, determining a likelihood further includes determining a difference between scores where the preselected portion of the body is stimulated and scores where the preselected portion of the body is not stimulated. In at least some embodiments of the system, non-transitory computer-readable medium, or method described above, determining a likelihood further includes randomizing the second entries with respect to the first entries to form a plurality of additional matrices. In at least some embodiments of the system, non-transitory computer-readable medium, or method described above, determining a likelihood further includes generating a distribution based on the matrix and the plurality of additional matrices.

In at least some embodiments of the system, non-transitory computer-readable medium, or method described above, obtaining the plurality of stimulation instances includes obtaining the plurality of stimulation instances from a plurality of patients.

A further embodiment is a system for identifying portions of a body in which electrical stimulation of that portion of the body to treat a condition or disorder affects at least one of at least one symptom of the condition or disorder, stimulation effect, or stimulation side effect. The system includes a computer processor configured and arranged to perform the following acts: obtaining N stimulation instances, where N is an integer greater than one, and, for each stimulation instance, an outcome score for each of at least one symptom of the condition or disorder, stimulation effect, or stimulation side effect; selecting M portions of the body, where M is an integer greater than one; estimating, for each of the N stimulation instances and for each of the M portions of the body, whether that portion of the body was stimulated during that stimulation instance; generating a matrix, where the matrix is either a) a N×M matrix with entries $a_{ij}$ or b) a M×N matrix with entries $a_{ji}$, where i is an integer ranging from 1 to N and corresponds to the $i^{th}$ stimulation instance and j is an integer ranging from 1 to M and corresponds to a $j^{th}$ portion of the body, where $a_{ij}$ or $a_{ji}$, respectively, is 0 if the $j^{th}$ portion of the body is not stimulated during the $i^{th}$ stimulation instance and is a non-zero value if the $j^{th}$ portion of the body is stimulated during the $i^{th}$ stimulation instance; determining a pseudoinverse of the matrix to estimate an influence of each of the M portions of the body on the outcome scores for the N stimulation instances; and storing or displaying the estimated influences to identify which portions of the body, when electrically stimulated, affect the at least one of the at least one symptom of the condition or disorder, stimulation effect, or stimulation side effect.

Another embodiment is a non-transitory computer-readable medium having processor-executable instructions for identifying portions of a body in which electrical stimulation of that portion of the body to treat a condition or disorder affects at least one of at least one symptom of the condition or disorder, stimulation effect, or stimulation side effect, the processor-executable instructions when installed onto a device enable the device to perform actions, including: obtaining N stimulation instances, where N is an integer greater than one, and, for each stimulation instance, an outcome score for each of at least one symptom of the condition or disorder, stimulation effect, or stimulation side effect; selecting M portions of the body, where M is an integer greater than one; estimating, for each of the N stimulation instances and for each of the M portions of the body, whether that portion of the body was stimulated during that stimulation instance; generating a matrix, where the matrix is either a) a N×M matrix with entries $a_{ij}$ or b) a M×N matrix with entries $a_{ji}$, where i is an integer ranging from 1 to N and corresponds to the $i^{th}$ stimulation instance and j is an integer ranging from 1 to M and corresponds to a $j^{th}$ portion of the body, where $a_{ij}$ or $a_{ji}$, respectively, is 0 if the $j^{th}$ portion of the body is not stimulated during the $i^{th}$ stimulation instance and is a non-zero value if the $j^{th}$ portion of the body is stimulated during the $i^{th}$ stimulation instance; determining a pseudoinverse of the matrix to estimate an influence of each of the M portions of the body on the outcome scores for the N stimulation instances; and storing or displaying the estimated influences to identify which portions of the body, when electrically stimulated, affect the at least one of the at least one symptom of the condition or disorder, stimulation effect, or stimulation side effect.

Yet another embodiment is a method for identifying portions of a body in which electrical stimulation of that portion of the body to treat a condition or disorder affects at least one of at least one symptom of the condition or disorder, stimulation effect, or stimulation side effect. The method includes obtaining N stimulation instances, where N is an integer greater than one, and, for each stimulation instance, an outcome score for each of at least one symptom of the condition or disorder, stimulation effect, or stimulation side effect; selecting M portions of the body, where M is an integer greater than one; estimating, for each of the N stimulation instances and for each of the M portions of the body, whether that portion of the body was stimulated during that stimulation instance; generating a matrix, where the matrix is either a) a N×M matrix with entries $a_{ij}$ or b) a M×N matrix with entries $a_{ji}$, where i is an integer ranging from 1 to N and corresponds to the $i^{th}$ stimulation instance and j is an integer ranging from 1 to M and corresponds to a $j^{th}$ portion of the body, where $a_{ij}$ or $a_{ji}$, respectively, is 0 if the $j^{th}$ portion of the body is not stimulated during the $i^{th}$ stimulation instance and is a non-zero value if the $j^{th}$ portion of the body is stimulated during the $i^{th}$ stimulation instance; determining a pseudoinverse of the matrix to estimate an influence of each of the M portions of the body on the outcome scores for the N stimulation instances; and storing or displaying the estimated influences to identify which portions of the body, when electrically stimulated, affect the at least one of the at least one symptom of the condition or disorder, stimulation effect, or stimulation side effect.

In at least some embodiments of the system, non-transitory computer-readable medium, or method described above, estimating, for each of the N stimulation instances and for each of the M portions of the body, whether that portion of the body was stimulated during that stimulation instance includes estimating, for each of the N stimulation instances and for each of the M portions of the body, whether that portion of the body was stimulated during that stimulation instance based on stimulation parameters used during the stimulation instance. In at least some embodiments of the system, non-transitory computer-readable medium, or method described above, obtaining N stimulation instances includes obtaining the N stimulation instances from a plurality of patients. In at least some embodiments of the system, non-transitory computer-readable medium, or method described above, further including generating a score vector including the outcome scores for the N stimulation instances. In at least some embodiments of the system, non-transitory computer-readable medium, or method described above, determining a pseudoinverse of the matrix includes determining an influence vector using the pseudo-inverse and score vector, where each entry in the influence vector corresponds to a different portion of the body. In at least some embodiments of the system, non-transitory computer-readable medium, or method described above, the entries of the influence vector indicate a relative influence of the corresponding portions of the body relative to the at least one symptom of the condition or disorder, stimulation effect, or stimulation side effect.

A further embodiment is a system for selecting or manipulating volumes of activation for electrical stimulation. The system includes a computer processor configured and arranged to perform the following acts: presenting a graphical user interface that includes at least one user-activatable button selected from a union button, an intersection button, or a subtraction button; displaying at least two volumes of activation; and in response to user activation of the at least one user-activatable button, displaying a union, an intersection, or a subtraction of at least two of the at least two volumes of activation.

Another embodiment is a non-transitory computer-readable medium having processor-executable instructions for selecting or manipulating volumes of activation for electrical stimulation, the processor-executable instructions when installed onto a device enable the device to perform actions, including: presenting a graphical user interface that includes at least one user-activatable button selected from a union button, an intersection button, or a subtraction button; displaying at least two volumes of activation; and in response to user activation of the at least one user-activatable button, displaying a union, an intersection, or a subtraction of at least two of the at least two volumes of activation.

Yet another embodiment is a method for selecting or manipulating volumes of activation for electrical stimulation. The method includes presenting a graphical user interface that includes at least one user-activatable button selected from a union button, an intersection button, or a subtraction button; displaying at least two volumes of activation; and in response to user activation of the at least one user-activatable button, displaying a union, an intersection, or a subtraction of at least two of the at least two volumes of activation.

In at least some embodiments of the system, non-transitory computer-readable medium, or method described above, the graphical user interface includes a union button, an intersection button, and a subtraction button. In at least some embodiments of the system, non-transitory computer-readable medium, or method described above, the volumes of activation further contain metadata associated with the volumes of activation. In at least some embodiments of the system, non-transitory computer-readable medium, or method described above, the graphical user interface further includes a search button. In at least some embodiments of the system, non-transitory computer-readable medium, or method described above, the acts further include in response to user activation of the search button, allowing the user to indicate one or more search terms; and searching metadata of a set of volumes of activation using the one or more search terms to identify one or more volumes of activation with metadata corresponding to the one or more search terms.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein:

FIG. 4 is a schematic flowchart of one embodiment of a method of identifying portions of a body for electrical stimulation, according to the invention;

FIG. 5A is a schematic illustration of one embodiment of a matrix for use in the method of FIG. 4, according to the invention;

FIG. 5B is a schematic illustration of one embodiment of a randomized matrix for use in the method of FIG. 4, according to the invention;

FIG. 5C is a schematic illustration of one embodiment of a distribution of values obtained using the method of FIG. 4, according to the invention;

FIG. 6 is a schematic flowchart of one embodiment of another method of identifying portions of a body for electrical stimulation, according to the invention;

FIG. 7A is a schematic illustration of one embodiment of a matrix for use in the method of FIG. 6, according to the invention;

FIG. 7B is a schematic illustration of one embodiment of a score vector for use in the method of FIG. 6, according to the invention;

DETAILED DESCRIPTION

The present invention is directed to the area of implantable electrical stimulation systems and methods of making and using the systems. The present invention is also directed to systems for determining regions of the body for stimulation or for selecting or manipulating volumes of activation, as well as methods of making and using the systems.

Suitable implantable electrical stimulation systems include, but are not limited to, a least one lead with one or more electrodes disposed on a distal end of the lead and one or more terminals disposed on one or more proximal ends of the lead. Leads include, for example, percutaneous leads and paddle leads. Examples of electrical stimulation systems with leads are found in, for example, U.S. Pat. Nos. 6,181,969; 6,516,227; 6,609,029; 6,609,032; 6,741,892; 7,244,150; 7,450,997; 7,672,734; 7,761,165; 7,783,359; 7,792,590; 7,809,446; 7,949,395; 7,974,706; 8,175,710; 8,224,450; 8,271,094; 8,295,944; 8,364,278; 8,391,985; and 8,688,235; and U.S. Patent Applications Publication Nos. 2007/0150036; 2009/0187222; 2009/0276021; 2010/0076535; 2010/0268298; 2011/0005069; 2011/0004267; 2011/0078900; 2011/0130817; 2011/0130818; 2011/0238129; 2011/0313500; 2012/0016378; 2012/0046710; 2012/0071949; 2012/0165911; 2012/0197375; 2012/0203316; 2012/0203320; 2012/0203321; 2012/0316615; 2013/0105071; and 2013/0197602, all of which are incorporated by reference. In the discussion below, a percutaneous lead will be exemplified, but it will be understood that the methods and systems described herein are also applicable to paddle leads.

A percutaneous lead for electrical stimulation (for example, deep brain or spinal cord stimulation) includes stimulation electrodes that can be ring electrodes or segmented electrodes that extend only partially around the circumference of the lead or any combination thereof. The segmented electrodes can be provided in sets of electrodes, with each set having electrodes circumferentially distributed about the lead at a particular longitudinal position. For illustrative purposes, the leads are described herein relative to use for deep brain stimulation, but it will be understood that any of the leads can be used for applications other than deep brain stimulation, including spinal cord stimulation, peripheral nerve stimulation, or stimulation of other nerves and tissues.

Figure 1:
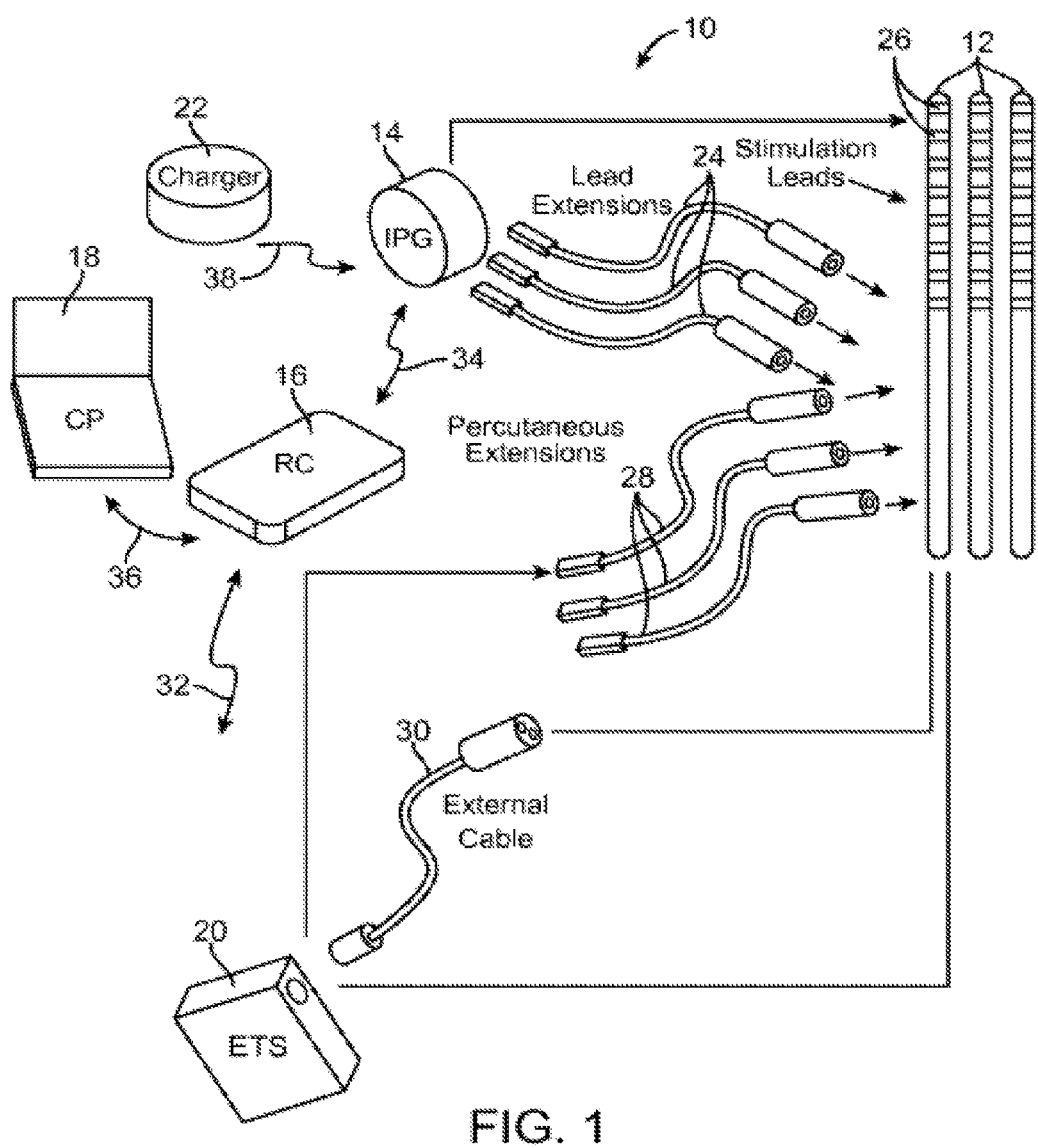
FIG. 1 is a schematic view of one embodiment of an electrical stimulation system, according to the invention.

Turning to FIG. 1, one embodiment of an electrical stimulation system 10 includes one or more stimulation leads 12 and an implantable pulse generator (IPG) 14. The system 10 can also include one or more of an external remote control (RC) 16, a clinician's programmer (CP) 18, an external trial stimulator (ETS) 20, or an external charger 22.

The IPG 14 is physically connected, optionally via one or more lead extensions 24, to the stimulation lead(s) 12. Each lead carries multiple electrodes 26 arranged in an array. The IPG 14 includes pulse generation circuitry that delivers electrical stimulation energy in the form of, for example, a pulsed electrical waveform (i.e., a temporal series of electrical pulses) to the electrode array 26 in accordance with a set of stimulation parameters. The implantable pulse generator can be implanted into a patient's body, for example, below the patient's clavicle area or within the patient's buttocks or abdominal cavity. The implantable pulse generator can have eight stimulation channels which may be independently programmable to control the magnitude of the current stimulus from each channel. In some embodiments, the implantable pulse generator can have more or fewer than eight stimulation channels (e.g., 4-, 6-, 16-, 32-, or more stimulation channels). The implantable pulse generator can have one, two, three, four, or more connector ports, for receiving the terminals of the leads.

The ETS 20 may also be physically connected, optionally via the percutaneous lead extensions 28 and external cable 30, to the stimulation leads 12. The ETS 20, which has similar pulse generation circuitry as the IPG 14, also delivers electrical stimulation energy in the form of, for example, a pulsed electrical waveform to the electrode array 26 in accordance with a set of stimulation parameters. One difference between the ETS 20 and the IPG 14 is that the ETS 20 is often a non-implantable device that is used on a trial basis after the neurostimulation leads 12 have been implanted and prior to implantation of the IPG 14, to test the responsiveness of the stimulation that is to be provided. Any functions described herein with respect to the IPG 14 can likewise be performed with respect to the ETS 20.

The RC 16 may be used to telemetrically communicate with or control the IPG 14 or ETS 20 via a uni- or bi-directional wireless communications link 32. Once the IPG 14 and neurostimulation leads 12 are implanted, the RC 16 may be used to telemetrically communicate with or control the IPG 14 via a uni- or bi-directional communications link 34. Such communication or control allows the IPG 14 to be turned on or off and to be programmed with different stimulation parameter sets. The IPG 14 may also be operated to modify the programmed stimulation parameters to actively control the characteristics of the electrical stimulation energy output by the IPG 14. The CP 18 allows a user, such as a clinician, the ability to program stimulation parameters for the IPG 14 and ETS 20 in the operating room and in follow-up sessions.

The CP 18 may perform this function by indirectly communicating with the IPG 14 or ETS 20, through the RC 16, via a wireless communications link 36. Alternatively, the CP 18 may directly communicate with the IPG 14 or ETS 20 via a wireless communications link (not shown). The stimulation parameters provided by the CP 18 are also used to program the RC 16, so that the stimulation parameters can be subsequently modified by operation of the RC 16 in a stand-alone mode (i.e., without the assistance of the CP 18).

For purposes of brevity, the details of the RC 16, CP 18, ETS 20, and external charger 22 will not be further described herein. Details of exemplary embodiments of these devices are disclosed in U.S. Pat. No. 6,895,280, which is expressly incorporated herein by reference. Other examples of electrical stimulation systems can be found at U.S. Pat. Nos. 6,181,969; 6,516,227; 6,609,029; 6,609,032; 6,741,892; 7,949,395; 7,244,150; 7,672,734; and U.S. Pat. Nos. 7,761,165; 7,974,706; 8,175,710; 8,224,450; and 8,364,278; and U.S. Patent Application Publication No. 2007/0150036, as well as the other references cited above, all of which are incorporated by reference.

Figure 2:
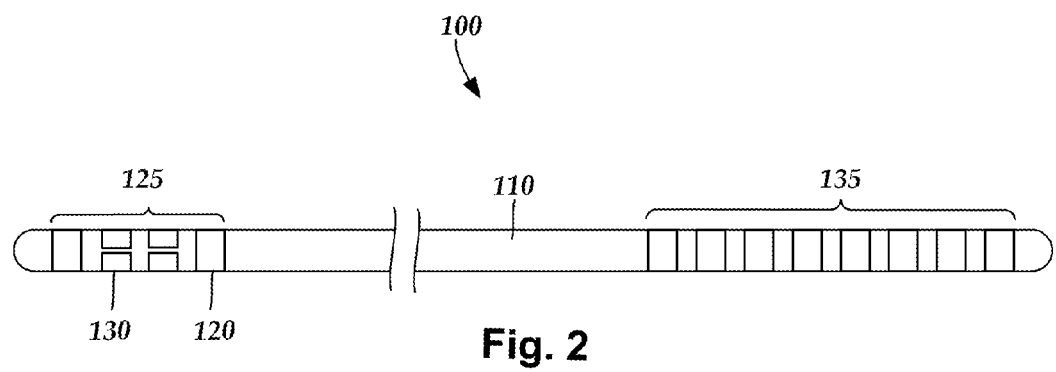
FIG. 2 is a schematic side view of one embodiment of an electrical stimulation lead, according to the invention.

FIG. 2 illustrates one embodiment of a lead 110 with electrodes 125 disposed at least partially about a circumference of the lead 110 along a distal end portion of the lead and terminals 135 disposed along a proximal end portion of the lead. The lead 110 can be implanted near or within the desired portion of the body to be stimulated such as, for example, the brain, spinal cord, or other body organs or tissues. In one example of operation for deep brain stimulation, access to the desired position in the brain can be accomplished by drilling a hole in the patient's skull or cranium with a cranial drill (commonly referred to as a burr), and coagulating and incising the dura mater, or brain covering. The lead 110 can be inserted into the cranium and brain tissue with the assistance of a stylet (not shown). The lead 110 can be guided to the target location within the brain using, for example, a stereotactic frame and a microdrive motor system. In some embodiments, the microdrive motor system can be fully or partially automatic. The microdrive motor system may be configured to perform one or more the following actions (alone or in combination): insert the lead 110, advance the lead 110, retract the lead 110, or rotate the lead 110.

In some embodiments, measurement devices coupled to the muscles or other tissues stimulated by the target neurons, or a unit responsive to the patient or clinician, can be coupled to the implantable pulse generator or microdrive motor system. The measurement device, user, or clinician can indicate a response by the target muscles or other tissues to the stimulation or recording electrode(s) to further identify the target neurons and facilitate positioning of the stimulation electrode(s). For example, if the target neurons are directed to a muscle experiencing tremors, a measurement device can be used to observe the muscle and indicate changes in tremor frequency or amplitude in response to stimulation of neurons. Alternatively, the patient or clinician can observe the muscle and provide feedback.

The lead 110 for deep brain stimulation can include stimulation electrodes, recording electrodes, or both. In at least some embodiments, the lead 110 is rotatable so that the stimulation electrodes can be aligned with the target neurons after the neurons have been located using the recording electrodes.

Stimulation electrodes may be disposed on the circumference of the lead 110 to stimulate the target neurons. Stimulation electrodes may be ring-shaped so that current projects from each electrode equally in every direction from the position of the electrode along a length of the lead 110. In the embodiment of FIG. 2, two of the electrodes 120 are ring electrodes 120. Ring electrodes typically do not enable stimulus current to be directed from only a limited angular range around of the lead. Segmented electrodes 130, however, can be used to direct stimulus current to a selected angular range around the lead. When segmented electrodes are used in conjunction with an implantable pulse generator that delivers constant current stimulus, current steering can be achieved to more precisely deliver the stimulus to a position around an axis of the lead (i.e., radial positioning around the axis of the lead). To achieve current steering, segmented electrodes can be utilized in addition to, or as an alternative to, ring electrodes.

The lead 100 includes a lead body 110, terminals 135, and one or more ring electrodes 120 and one or more sets of segmented electrodes 130 (or any other combination of electrodes). The lead body 110 can be formed of a biocompatible, non-conducting material such as, for example, a polymeric material. Suitable polymeric materials include, but are not limited to, silicone, polyurethane, polyurea, polyurethane-urea, polyethylene, or the like. Once implanted in the body, the lead 100 may be in contact with body tissue for extended periods of time. In at least some embodiments, the lead 100 has a cross-sectional diameter of no more than 1.5 mm and may be in the range of 0.5 to 1.5 mm. In at least some embodiments, the lead 100 has a length of at least 10 cm and the length of the lead 100 may be in the range of 10 to 70 cm.

The electrodes 125 can be made using a metal, alloy, conductive oxide, or any other suitable conductive biocompatible material. Examples of suitable materials include, but are not limited to, platinum, platinum iridium alloy, iridium, titanium, tungsten, palladium, palladium rhodium, or the like. Preferably, the electrodes are made of a material that is biocompatible and does not substantially corrode under expected operating conditions in the operating environment for the expected duration of use.

Each of the electrodes can either be used or unused (OFF). When the electrode is used, the electrode can be used as an anode or cathode and carry anodic or cathodic current. In some instances, an electrode might be an anode for a period of time and a cathode for a period of time.

Deep brain stimulation leads may include one or more sets of segmented electrodes. Segmented electrodes may provide for superior current steering than ring electrodes because target structures in deep brain stimulation are not typically symmetric about the axis of the distal electrode array. Instead, a target may be located on one side of a plane running through the axis of the lead. Through the use of a radially segmented electrode array ("RSEA"), current steering can be performed not only along a length of the lead but also around a circumference of the lead. This provides precise three-dimensional targeting and delivery of the current stimulus to neural target tissue, while potentially avoiding stimulation of other tissue. Examples of leads with segmented electrodes include U.S. Patent Application Publications Nos. 2010/0268298; 2011/0005069; 2011/0130803; 2011/0130816; 2011/0130817; 2011/0130818; 2011/0078900; 2011/0238129; 2012/0016378; 2012/0046710; 2012/0071949; 2012/0165911; 2012/197375; 2012/0203316; 2012/0203320; 2012/0203321, all of which are incorporated herein by reference.

An electrical stimulation lead can be implanted in the body of a patient (for example, in the brain or spinal cord of the patient) and used to stimulate surrounding tissue. It is useful to estimate the effective region of stimulation (often called a volume of activation (VOA) or stimulation field model (SFM)) given the position of the lead and its electrodes in the patient's body and the stimulation parameters used to generate the stimulation. Any suitable method for determining the VOA and for graphically displaying the VOA relative to patient anatomy can be used including those described in, for example, U.S. Pat. Nos. 8,326,433; 8,675,945; 8,831,731; 8,849,632; and 8,958,615; U.S. Patent Application Publications Nos. 2009/0287272; 2009/0287273; 2012/0314924; 2013/0116744; 2014/0122379; and 2015/0066111; and U.S. Provisional Patent Application Ser. No. 62/030,655, all of which are incorporated herein by reference. Several of these references also disclose methods and systems for registering an atlas of body structures to imaged patient physiology.

A VOA can be determined based on a set of stimulation parameters input into the system. The VOA can then be modified by the user by modifying the stimulation parameters and determining the new VOA from the modified stimulation parameters. This allows the user to tailor the stimulation volume.

Figure 3:
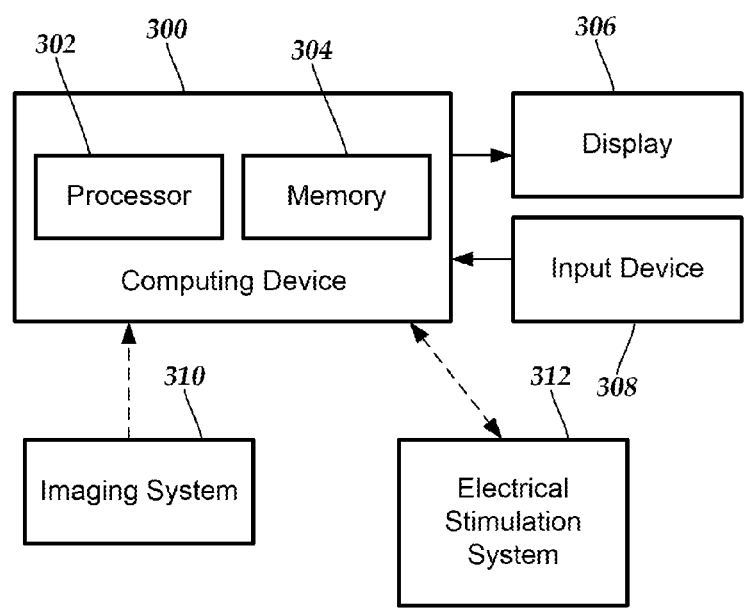
FIG. 3 is a schematic block diagram of one embodiment of a system for determining stimulation parameters, according to the invention.

FIG. 3 illustrates one embodiment of a system for determining electrical stimulation parameters. The system can include a computing device 300 or any other similar device that includes a processor 302 and a memory 304, a display 306, an input device 308, and, optionally, the electrical stimulation system 312. The system 300 may also optionally include one or more imaging systems 310.

The computing device 300 can be a computer, tablet, mobile device, or any other suitable device for processing information. The computing device 300 can be local to the user or can include components that are non-local to the computer including one or both of the processor 302 or memory 304 (or portions thereof). For example, in some embodiments, the user may operate a terminal that is connected to a non-local computing device. In other embodiments, the memory can be non-local to the user.

The computing device 300 can utilize any suitable processor 302 including one or more hardware processors that may be local to the user or non-local to the user or other components of the computing device. The processor 302 is configured to execute instructions provided to the processor.

Any suitable memory 304 can be used for the computing device 302. The memory 304 illustrates a type of computer-readable media, namely computer-readable storage media.

Computer-readable storage media may include, but is not limited to, nonvolatile, non-transitory, removable, and non-removable media implemented in any method or technology for storage of information, such as computer readable instructions, data structures, program modules, or other data. Examples of computer-readable storage media include RAM, ROM, EEPROM, flash memory, or other memory technology, CD-ROM, digital versatile disks ("DVD") or other optical storage, magnetic cassettes, magnetic tape, magnetic disk storage or other magnetic storage devices, or any other medium which can be used to store the desired information and which can be accessed by a computing device.

Communication methods provide another type of computer readable media; namely communication media. Communication media typically embodies computer-readable instructions, data structures, program modules, or other data in a modulated data signal such as a carrier wave, data signal, or other transport mechanism and include any information delivery media. The terms "modulated data signal," and "carrier-wave signal" includes a signal that has one or more of its characteristics set or changed in such a manner as to encode information, instructions, data, and the like, in the signal. By way of example, communication media includes wired media such as twisted pair, coaxial cable, fiber optics, wave guides, and other wired media and wireless media such as acoustic, RF, infrared, and other wireless media.

The display 306 can be any suitable display device, such as a monitor, screen, display, or the like, and can include a printer. The input device 308 can be, for example, a keyboard, mouse, touch screen, track ball, joystick, voice recognition system, or any combination thereof, or the like.

One or more imaging systems 310 can be used including, but not limited to, MRI, CT, ultrasound, or other imaging systems. The imaging system 310 may communicate through a wired or wireless connection with the computing device 300 or, alternatively or additionally, a user can provide images from the imaging system 310 using a computer-readable medium or by some other mechanism.

The electrical stimulation system 312 can include, for example, any of the components illustrated in FIG. 1. The electrical stimulation system 312 may communicate with the computing device 300 through a wired or wireless connection or, alternatively or additionally, a user can provide information between the electrical stimulation system 312 and the computing device 300 using a computer-readable medium or by some other mechanism. In some embodiments, the computing device 300 may include part of the electrical stimulation system, such as, for example, the IPG, CP, RC, ETS, or any combination thereof.

The methods and systems described herein may be embodied in many different forms and should not be construed as limited to the embodiments set forth herein. Accordingly, the methods and systems described herein may take the form of an entirely hardware embodiment, an entirely software embodiment or an embodiment combining software and hardware aspects. Systems referenced herein typically include memory and typically include methods for communication with other devices including mobile devices. Methods of communication can include both wired and wireless communications methods. Wired communication can include communication over a twisted pair, coaxial cable, fiber optics, wave guides, or the like, or any combination thereof. Wireless communication can include RF, infrared, optical, acoustic, near field communication, Bluetooth™, or the like, or any combination thereof.

It would useful to determine desirable regions for delivery of electrical stimulation to provide a therapeutic effect or to determine regions to avoid stimulating to reduce or avoid a side effect. In at least some instances, when an electrical stimulation lead is implanted in a patient, the patient undergoes an assessment in which different sets of stimulation parameters are tested and assessed based on some rating scale (for example, the Unified Parkinson's Disease Rating Scale (UPDRS)).

In addition, in at least some instances, the location of the implanted lead within the patient's body can be determined using postoperative imaging (for example, by a CT scan). The location of the lead, and its corresponding electrodes, and the stimulation parameters can be used to estimate the volume of tissue that is stimulated using those parameters.

This data from a single patient or from multiple patients can be evaluated to identify which portions of body (for example, portions of the brain), when electrically stimulated, are likely to affect at least one symptom of a treated condition or disorder or produce a stimulation effect or produce a stimulation side effect. When data from multiple patients is evaluated, the patients may be drawn from the general population or can be selected based on one or more criteria including, but not limited to, the condition or disorder being treated, age, gender, residence, weight, ethnicity, nationality, or the like or any combination thereof.

By understanding which portions of the body, when electrically stimulated, are likely to produce an effect on a symptom, some other stimulation effect, or a side effect, a practitioner can select stimulation parameters that are likely to stimulate (or not simulate) a portion of the body. It will be recognized that these parameters represent estimates and, when implemented, may be revised or modified upon actual testing in the patient's body.

The present invention is directed, at least in part, to evaluating data from patients to predict which portions of the body can be stimulated to produce an effect on a symptom, a stimulation effect, or a stimulation side effect. In some embodiments, a permutation test can be used to evaluate multiple actual stimulation instances and associated scores to evaluate which portions of the body are likely to produce an effect on a symptom, a stimulation effect, or a side effect when stimulated.

FIG. 4 outlines one embodiment of a method for identifying portions of a body in which electrical stimulation to treat a condition or disorder is likely to affect at least one symptom, stimulation effect, or stimulation side effect. In step 402, multiple actual stimulation instances are obtained. In at least some embodiments, each stimulation instance includes a set of stimulation parameters (for example, pulse width, pulse duration, pulse frequency, pulse amplitude, and the like), values for those stimulation parameters, and at least one score directed toward at least one symptom, stimulation effect, or stimulation side effect. As used herein, the term "stimulation parameter" is used to indicate the a categorization of a parameter and the terms "stimulation parameter value" or "value" are used to indicated the actual value (for example, a numerical value) for the particular stimulation parameter.

In at least some embodiments, each stimulation instance includes the same stimulation parameters, although one or more of the stimulation parameter values may be different. In other embodiments, a different set of stimulation parameters may be associated with one or more of the stimulation instances. For example, some stimulation instances may include a stimulation pulse width while other stimulation instances fail to include the stimulation pulse width.

In at least some embodiments, each stimulation instance includes score(s) for the same symptom(s), stimulation effect(s), or stimulation side effect(s). In other embodiments, different stimulation instances may have score(s) for different sets of symptom(s), stimulation effect(s), or stimulation side effect(s).

The stimulation instances can be from a single patient or can be from multiple patients. In at least some embodiments, each stimulation instance is directed to treating the same condition or disorder. In other embodiments, different stimulation instances may be directed to treating different conditions or disorders which may be related or unrelated.

In step 404, the stimulation parameters of each stimulation instance are used to estimate a region of the body that is stimulated by these stimulation parameters. These estimates can include, for example, estimates of axonal activation, estimates of cell bodies that are activated, estimates of fiber pathways that are activated, and the like or any combination thereof. In at least some instances, the estimate is called a value of activation (VOA) or stimulation field model (SFM) Examples of suitable methods for making these estimations include, but are not limited to, those described in U.S. Pat. Nos. 8,326,433; 8,675,945; 8,831,731; 8,849,632; and 8,958,615; U.S. Patent Application Publications Nos. 2009/0287272; 2009/0287273; 2012/0314924; 2013/0116744; 2014/0122379; and 2015/0066111; and U.S. Provisional Patent Application Ser. No. 62/030,655, all of which are incorporated herein by reference. It will be understood that other methods of estimating the stimulation region that do not use the stimulation parameters can also be employed.

In other embodiments, the stimulation instances are provided to the system with an indication of the stimulation region. In such embodiments, the system may not need to computer or estimate the stimulation regions.

As the stimulation regions are computed or estimated, the stimulation regions are optionally transformed to a common space using the patients' imaging data, using an anatomical atlas, or using any other suitable method for providing a common reference frame for the stimulation regions. This enables overlay of all stimulation regions for all stimulation instances into the common reference frame.

In step 406, the likelihood that stimulation of each of one or more selected portions of the body will affect a symptom, stimulation effect, or stimulation side effect is analyzed. In at least some embodiments, a body area of interest is divided into volume elements ("voxels"). Each voxel can have a same volume or the voxels can have different volumes. In some embodiments, voxels are selected so that each voxel is only associated with a single anatomical structure (for example, a single brain structure). The voxels may cover the entire area of interest or only portions of the area of interest. The voxels can be contiguous with each other or non-contiguous.

A permutation test is used to determine a likelihood whether stimulation of a particular voxel contributes to the score for a particular symptom, stimulation effect, or stimulation side effect. To illustrate one method of analyzing the likelihood that stimulation of a voxel (which correspond to a portion of the body, as described above) will affect a particular symptom, stimulation effect, or stimulation side effect using a permutation test, a matrix is created for that voxel and for that symptom, stimulation effect, or stimulation side effect. As an example, a 2 column matrix 500 can be created for each voxel for a single symptom, stimulation effect, or stimulation side effect, as illustrated in FIG. 5A. Each row of this matrix corresponds to a different stimulation instance. In the illustrated example, there are N stimulation instances. The entry for each row, $A_n$, in the first column of this matrix is 0 or 1 depending on whether the voxel was stimulated (i.e., active) or not stimulated (i.e., inactive), respectively, for this stimulation instance. The entry for each row, $S_n$, in the second column is the corresponding score that indicates, for example, the improvement or worsening of the particular symptom, stimulation effect, or stimulation side effect for that stimulation instance. It will be recognized that the rows can instead be columns and columns can then be rows. A similar matrix can be formed for each individual voxel. In addition, similar matrices can be used to investigate other symptoms, stimulation effects, or stimulation side effects.

A statistical analysis is performed using a permutation test to assess whether a voxel's state of activation is influential on the symptom, stimulation effect, or stimulation side effect. As an example, the permutation test proceeds as follows: the difference in average scores (or difference in scores or any other suitable measure) between the active (first column=1) and inactive (first column=0) states for each voxel is determined. Then, the entries in the first column (or, alternatively, the second column) in the matrix are randomized to produce a new matrix 500', as illustrated in FIG. 5B where x, y, z, and w are different random integers in the range from 1 to N. The difference in average scores between the "active" (first column=1) and "inactive" (first column=0) states is again calculated for this randomized matrix. This randomization and difference determination process is repeated many times (for example, at least 100, 500, 1000, 2000, 2500, 5000, or more times). The resulting differences can be plotted as a distribution 502 of the difference in scores between the "active" states (first column=1) and "inactive" states (first column=0), as illustrated in FIG. 5C. The permutation test is performed under the null hypothesis that "the voxel's state (active or inactive) does not influence the scores". The observed value 504 of the difference between scores in the actual active and inactive state (which is the first computed difference) is compared with this distribution. If the observed value is unlikely to occur from this distribution, the null hypothesis is declared invalid (i.e. the voxel does influence the scores). If the null hypothesis is declared invalid, it is likely that the voxel does influence the scores for the selected symptom, stimulation effect, or stimulation side effect. The likelihood of the observed value occurring in the distribution can be used to determine or estimate a qualitative or quantitative likelihood that the voxel influences the scores for the selected symptom, stimulation effect, or stimulation side effect.

A permutation test can be performed for each voxel of interest with respect to the selected symptom, stimulation effect, or stimulation side effect. This process separates voxels between those that are likely influential with respect to the selected symptom, stimulation effect, or stimulation side effect and those that are not likely influential. One or more of the influential voxels can form a target volume for the given symptom, stimulation effect, and stimulation side effect. A threshold criterion 506, or multiple threshold criteria, (where the observed value 504 is outside the threshold criterion) can be used to extract voxels at different levels of significance.

The importance of using a permutation test here (as opposed to a t-test) is that a permutation test provides a robust, non-parametric approach to determine statistical significance of the influence of a voxel on a particular symptom, stimulation effect, and stimulation side effect.

In step 408, the this analysis of the voxels and their influence on the selected symptom, stimulation effect, stimulation side effect can be stored on a computer or other storage device and can be displayed for review by a practitioner. The process can be repeated for additional voxels and for additional symptoms, stimulation effects, or stimulation side effects. A practitioner can utilize the results of these analyses to identify portions of the body that could be stimulated to produce a desirable treatment of one or more symptoms or desirable stimulation effects or portions of the body to avoid stimulating to reduce or eliminate one or more side effects.

A user can then use the analysis of the voxels to identify a proposed stimulation region and then select stimulation parameters that will stimulate that region. In at least some embodiments, the stimulation parameters can be provided to an implantable pulse generator or external trial stimulator for generating electrical stimulation. The electrical stimulation can be provided to a patient using any suitable electrical stimulation system including the stimulation system illustrated in FIG. 1.

In some embodiments, a pseudoinverse is used to evaluate multiple actual stimulation instances and associated scores to evaluate which portions of the body, when stimulated, contribute to an outcome. The outcome can represent treatment of a symptom, disease, or disorder; production of a stimulation effect; production of a stimulation side effect; or the like.

FIG. 6 outlines one embodiment of a method for identifying evaluate which portions of the body, when stimulated, are likely to affect at least one symptom, stimulation effect, or stimulation side effect. In step 602, multiple actual stimulation instances are obtained. Each stimulation instance includes a set of stimulation parameters (for example, pulse width, pulse duration, pulse frequency, pulse amplitude, and the like), values for those stimulation parameters, and at least one score directed toward an outcome such as treatment of at least one symptom, disease, or disorder; production of a stimulation effect; or production of a stimulation side effect. As used herein, the term "stimulation parameter" is used to indicate the a categorization of a parameter and the terms "stimulation parameter value" or "value" are used to indicated the actual value (for example, a numerical value) for the particular stimulation parameter.

In at least some embodiments, each stimulation instance includes the same stimulation parameters, although one or more of the stimulation parameter values may be different. In other embodiments, a different set of stimulation parameters may be associated with one or more of the stimulation instances. For example, some stimulation instances may include a stimulation pulse width while other stimulation instances fail to include the stimulation pulse width.

In at least some embodiments, each stimulation instance includes score(s) for the same symptom(s), stimulation effect(s), or stimulation side effect(s). In other embodiments, different stimulation instances may have score(s) for different sets of symptom(s), stimulation effect(s), or stimulation side effect(s).

The stimulation instances can be from a single patient or can be from multiple patients. In at least some embodiments, each stimulation instance is directed to treating the same condition or disorder. In other embodiments, different stimulation instances may be directed to treating different conditions or disorders which may be related or unrelated.

In step 604, the stimulation parameters of each stimulation instance are used to estimate a region of the body that is stimulated by these stimulation parameters. These estimates can include, for example, estimates of axonal activation, estimates of cell bodies that are activated, estimates of fiber pathways that are activated, and the like or any combination thereof. In at least some instances, the estimate is called a value of activation (VOA) or stimulation field model (SFM) Examples of suitable methods for making these estimations include, but are not limited to, those described in U.S. Pat. Nos. 8,326,433; 8,675,945; 8,831,731; 8,849,632; and 8,958,615; U.S. Patent Application Publications Nos. 2009/0287272; 2009/0287273; 2012/0314924; 2013/0116744; 2013/0116748; 2014/0122379; and 2015/0066111; and U.S. Provisional Patent Application Ser. No. 62/030,655, all of which are incorporated herein by reference. It will be understood that other methods of estimating the stimulation region that do not use the stimulation parameters can also be employed.

In other embodiments, the stimulation instances are provided to the system with an indication of the stimulation region. In such embodiments, the system may not need to computer or estimate the stimulation regions.

As the stimulation regions are computed or estimated, the stimulation regions are optionally transformed to a common space using the patients' imaging data, using an anatomical atlas, or using any other suitable method for providing a common reference frame for the stimulation regions. This enables overlay of all stimulation regions for all stimulation instances into the common reference frame.

In step 606, an analysis is preformed to identify portions of the body that, when stimulated, will likely affect a symptom, stimulation effect, or stimulation side effect. In at least some embodiments, a body area of interest is divided into volume elements ("voxels"). Each voxel can have a same volume or the voxels can have different volumes. In some embodiments, voxels are selected so that each voxel is only associated with a single anatomical structure (for example, a single brain structure). The voxels may cover the entire area of interest or only portions of the area of interest. The voxels can be contiguous with each other or non-contiguous.

To illustrate one method of analyzing which voxels (which correspond to portions of the body), when stimulated, will likely affect a particular symptom, stimulation effect, or stimulation side effect using a pseudoinverse calculation, a matrix is created with each voxel representing a column and each stimulation instance representing a row. (It will be understood that, alternatively, the voxels could be assigned as rows and the stimulation instances could be assigned as columns.) For N stimulation instances and M voxels (i.e., portions of the body), the matrix is a N×M matrix, A, with entries $a_{ij}$ (or a M×N matrix with entries $a_{ji}$ if the alternative assignment of rows and columns is used) where i is an integer ranging from 1 to N and corresponds to the $i^{th}$ stimulation instance and j is an integer ranging from 1 to M and corresponds to a $i^{th}$ portion of the body, as illustrated in FIG. 7A. In this embodiment, $a_{ij}$ is 0 if the $j^{th}$ portion of the body is not stimulated during the $i^{th}$ stimulation instance and is a non-zero value (for example, one) if the $j^{th}$ portion of the body is stimulated during the $i^{th}$ stimulation instance.

In addition, a one column vector, S, of the scores is generated with entries $S_i$ which is the score (i.e., outcome) for the $i^{th}$ stimulation instance, as illustrated in FIG. 7B. Based on these definitions of S and A, S=A·I, where I is a one column influence vector which indicates that influence that stimulation of each voxel has on the observed outcomes. The influence vector can then be determined as I=$A^+$·S, wherein $A^+$ is the pseudoinverse of A. Methods for calculating, estimating, or otherwise determining the pseudoinverse, $A^+$, of A are known and any suitable method can be used.

Figure 8A:
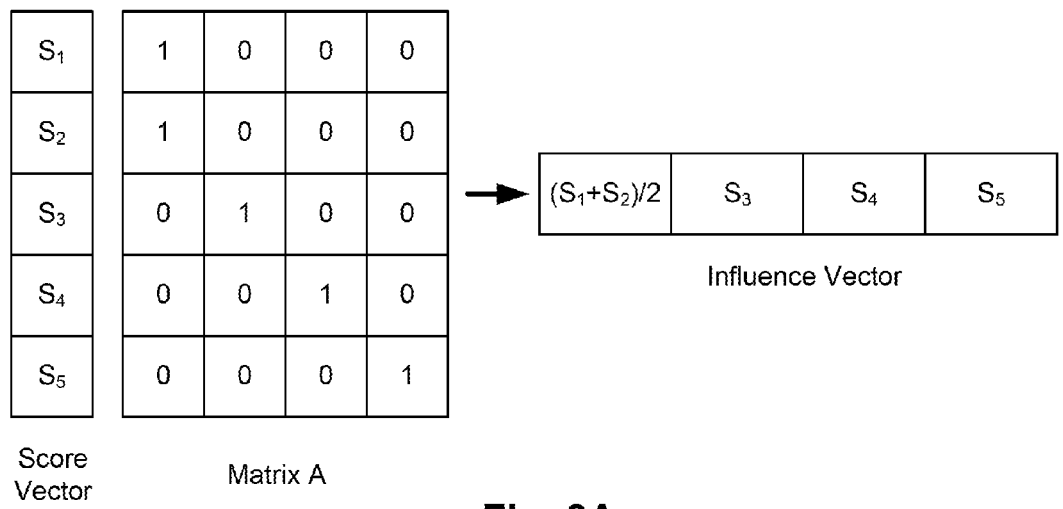
FIG. 8A is a schematic illustration of one embodiment of a determination of an influence vector using the method of FIG. 6, according to the invention.

FIG. 8A illustrates one example of a 5×4 matrix A which represents five stimulation instances and four voxels. The matrix A has been filled out to indicate which voxels are stimulated ($a_{ij}$=1) or not stimulated ($a_{ij}$=0) during each stimulation instance. The example also includes a score vector S with scores $S_1$ to $S_5$. Using the pseudoinverse of A, an influence vector can be obtained, as illustrated in FIG. 8A. The entries in the influence vector correspond to the respective voxels and can be used to indicate which voxels are most likely to influence an overall outcome with respect to a particular symptom, stimulation effect, or stimulation side effect.

Figure 8B:
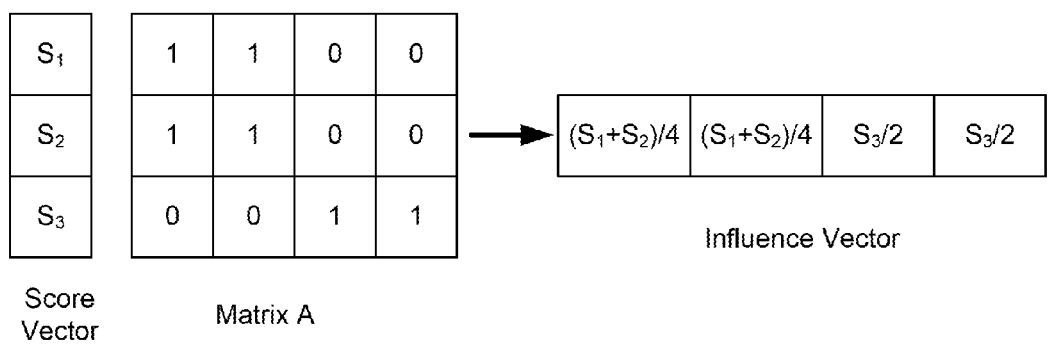
FIG. 8B is a schematic illustration of one embodiment of another determination of an influence vector using the method of FIG. 6, according to the invention.

FIG. 8B illustrates one example of a 3×4 matrix A which represents three stimulation instances and four voxels. The matrix A has been filled out to indicate which voxels are stimulated ($a_{ij}$=1) or not stimulated ($a_{ij}$=0) during each stimulation instance. The example also includes a score vector S with scores $S_1$ to $S_3$. Using the pseudoinverse of A, an influence vector can be obtained, as illustrated in FIG. 8B. The entries in the influence vector correspond to the respective voxels and can be used to indicate which voxels are most likely to influence an overall outcome with respect to a particular symptom, stimulation effect, or stimulation side effect.

In step 608, the analysis of the voxels and their influence on the selected symptom, stimulation effect, stimulation side effect can be stored on a computer or other storage device and can be displayed for review by a practitioner. The process can be repeated for additional voxels and for additional symptoms, stimulation effects, or stimulation side effects. A practitioner can utilize the results of these analyses to identify portions of the body that could be stimulated to produce a desirable treatment of one or more symptoms or desirable stimulation effects or portions of the body to avoid stimulating to reduce or eliminate one or more side effects.

A user can then use the analysis of the voxels to identify a proposed stimulation region and then select stimulation parameters that will stimulate that region. In at least some embodiments, the stimulation parameters can be provided to an implantable pulse generator or external trial stimulator for generating electrical stimulation. The electrical stimulation can be provided to a patient using any suitable electrical stimulation system including the stimulation system illustrated in FIG. 1.

Figure 9A:
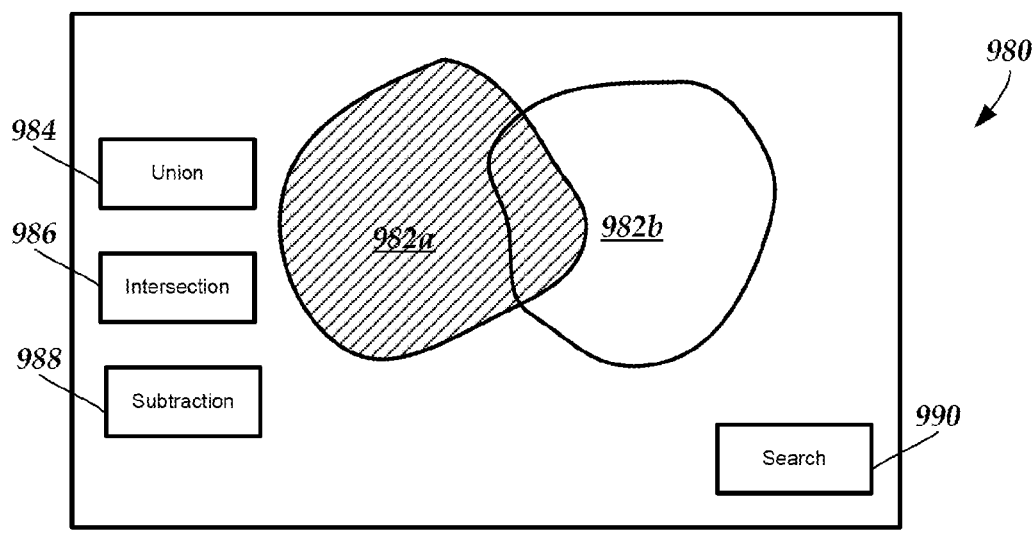
FIG. 9A is a schematic illustration of one embodiment of a graphical user interface for selecting or manipulating volumes of activation, according to the invention.

A graphical user interface (GUI) can be used to visualize and modify one or more VOAs. FIG. 9A shows a GUI 980 according to an example embodiment of the present invention. The illustrated GUI 980 is simplified for purposes of illustration and illustrates two VOAs 982*a*, 982*b* and several buttons 984, 986, 988, 990 for user interaction to activate system functions. It will be understood, however, that the GUI can include additional features including, but not limited to, one or more of a representation of patient body structures (e.g., portions of the patient brain or any other anatomical region) which may obtained from images or represent idealized structures based on an atlas or the like; a representation of a lead or lead electrodes; additional buttons or other structures for initiating GUI functions; information regarding the patient, body structures, VOAs, stimulation parameters, or the like; and so forth. Examples of GUIs that can be modified to include the functions described herein can be found at, for example, U.S. Pat. Nos. 8,326,433; 8,675,945; 8,831,731; 8,849,632; and 8,958,615; U.S. Patent Application Publications Nos. 2009/0287272; 2009/0287273; 2012/0314924; 2013/0116744; 2013/0116748; 2014/0122379; and 2015/0066111; and U.S. Provisional Patent Application Ser. No. 62/030,655, all of which are incorporated herein by reference.

The displayed VOAs can be two dimensional (as illustrated in FIG. 9A) or three dimensional. In at least some embodiments, the GUI is user-interactive, e.g., by point and click using an input device such as a mouse, stylus, or even the user's finger, or by keyboard manipulation, for selecting or deselecting buttons and the like.

The illustrated GUI includes a union button 985, an intersection button 986, a subtraction button 988, and a search button 990. Other GUIs can include any combination of these buttons and GUI elements as described in the references cited above.

In some embodiments, the system can allow visualization of VOA's that can be calculated based on stimulation parameters and, optionally, are associated with a patient. The VOA's can be tagged with metadata that can be searched. Examples of metadata include, but are not limited to, demographic information (e.g., gender, age, race, nationality, height, weight, or the like of a patient associated with the VOA), diagnosis, clinician notes, lead position, stimulated body structures, or the like. The VOA's from multiple patients may be maintained in a database and, at least in some systems, the VOA's may be searchable based on one or more metadata items. In at least some embodiments, the GUI 980 includes a search button 990 that initiates a search procedure that allows the user to input or select search parameters, such as the metadata indicated above, in order to find and display one or more VOAs.

Figure 9B:
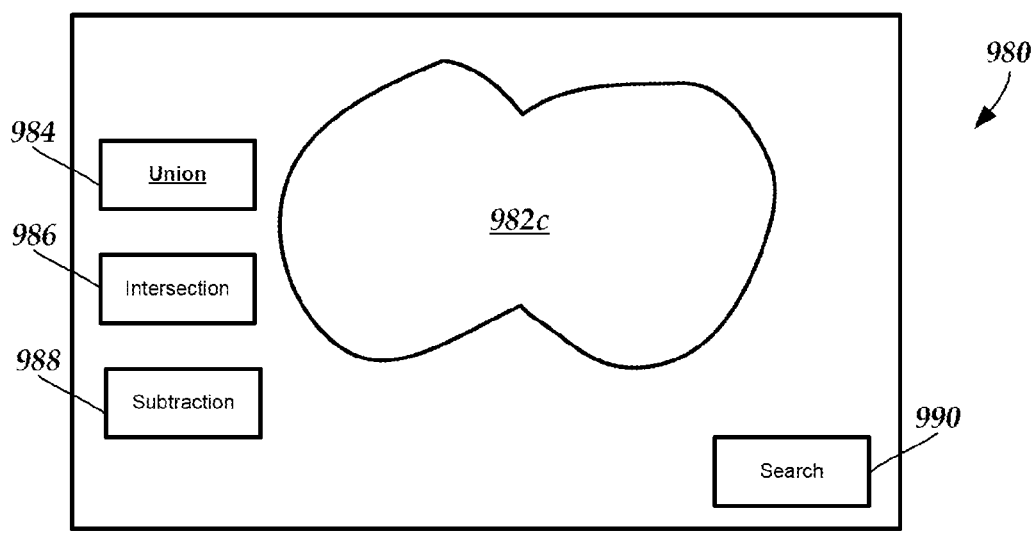
FIG. 9B is a schematic illustration of the graphical user interface of FIG. 9A in which the union of two volumes of activation is presented, according to the invention.
Figure 9C:
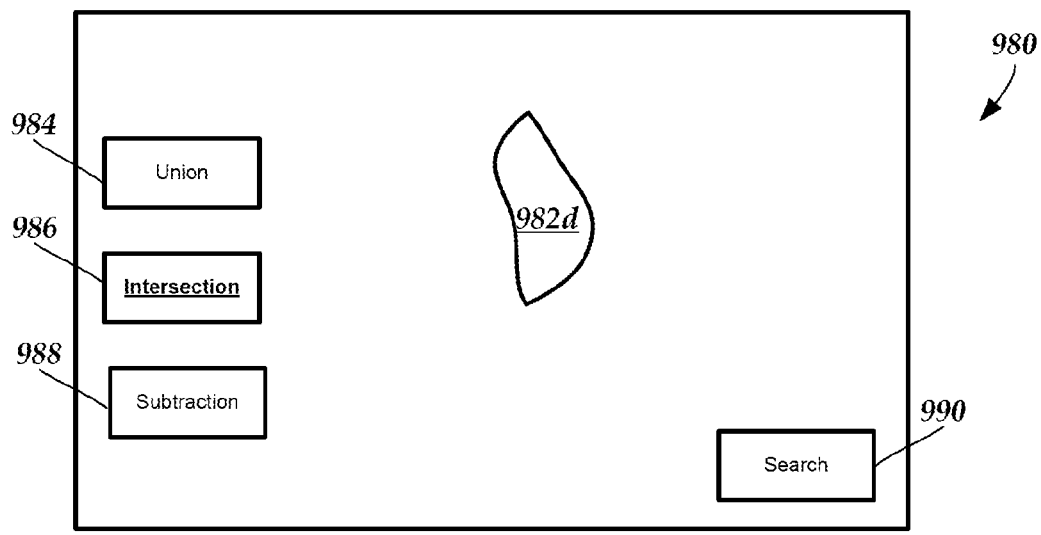
FIG. 9C is a schematic illustration of the graphical user interface of FIG. 9A in which the intersection of two volumes of activation is presented, according to the invention.
Figure 9D:
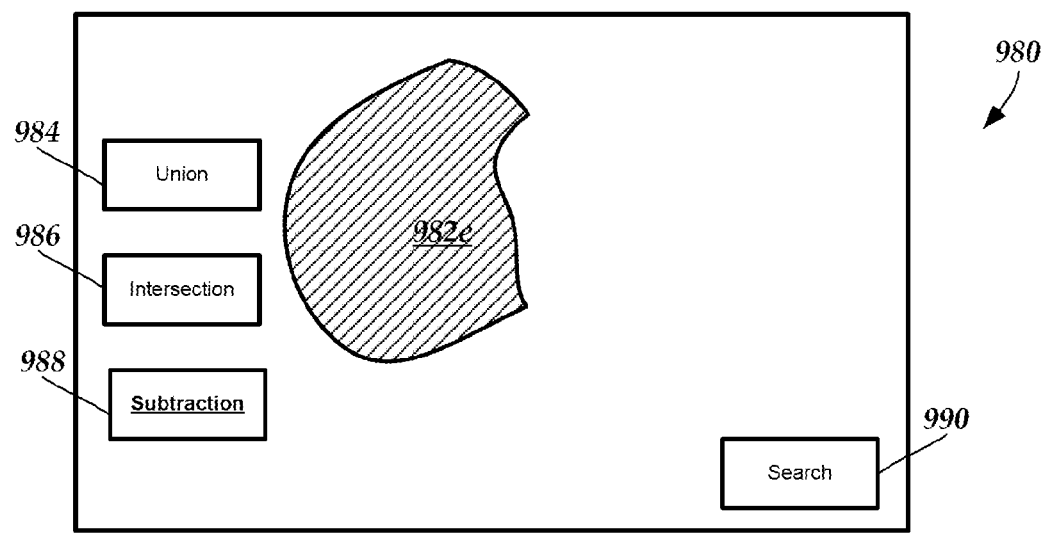
FIG. 9D is a schematic illustration of the graphical user interface of FIG. 9A in which the subtraction of one volume of activation from another volume of activation is presented, according to the invention.

In some embodiments, the system may also allow the user to perform operations on VOAs. For example, a GUI 980 can include a union button 984 to form the union 982*c* of two or more VOAs 982*a*, 982*b* (FIG. 9A) as illustrated in FIG. 9B, an intersection button 986 to form the intersection 982*d* of two or more VOAs 982*a*, 982*b* (FIG. 9A) as illustrated in FIG. 9C, or a subtraction button to subtract one VOA 982*b* (FIG. 9A) from another VOA 982*a* (FIG. 9A) to form a new VOA 982*e*, as illustrated in FIG. 9D of a VOA, or any combination of these buttons. The resulting modified VOA can be displayed in a GUI. For example, the user may request which voxels are common to two or more VOAs and the GUI can display the intersection of the two or more VOAs. As another example, the user may request display of the union of two or more VOAs. As yet another example, the user may request the intersection of VOA A with VOA B followed by the union of this result with VOA C. In a further example, the user may request the union of VOA A with VOA B followed by the intersection with VOA C.

In at least some embodiments, if an intersection of two or more VOAs is requested, the system may also determine and display an indication of what fraction or percentage of one or more of the VOAs remains in the intersection. In at least some embodiments, if an intersection of two or more VOAs is requested, the system may also determine and display an indication of what fraction or percentage of one or more of the VOAs is excluded from the intersection. In at least some embodiments, if one VOA is subtracted from another VOA, the system may also determine and display an indication of what fraction or percentage of one or more of the VOAs remains. In at least some embodiments, if one VOA is subtracted from another VOA, the system may also determine and display an indication of what fraction or percentage of one or more of the VOAs is removed or excluded from the result. Examples of other calculations that can be performed for combinations of VOAs can be found in U.S. Patent Application Publication No. 2013/0116748, incorporated herein by reference.

In at least some embodiments, the union, intersection, or subtraction of two or more VOAs can also be displayed with one or more anatomic structures (for example, brain structures), such as those obtained using an atlas or using images from the patient or from some other source. In at least some embodiments, if the union, intersection, or subtraction of two or more VOAs includes at least a threshold amount (for example, at least 25%, 33%, 50%, 67%, 75%, or more) of a particular anatomic structure, the resulting VOA may be modified, either automatically, manually, or with approval by the user, to include the anatomic structure.

It will be understood that the system can include one or more of the methods and GUIs described hereinabove with respect to FIGS. 4-9D in any combination. The methods, systems, and GUIs described herein may be embodied in many different forms and should not be construed as limited to the embodiments set forth herein. Accordingly, the methods, systems, and GUIs described herein may take the form of an entirely hardware embodiment, an entirely software embodiment or an embodiment combining software and hardware aspects. The methods described herein can be performed using any type of processor or any combination of processors where each processor performs at least part of the process.

It will be understood that each block of the flowchart illustrations, and combinations of blocks in the flowchart illustrations and methods disclosed herein, can be implemented by computer program instructions. These program instructions may be provided to a processor to produce a machine, such that the instructions, which execute on the processor, create means for implementing the actions specified in the flowchart block or blocks disclosed herein. The computer program instructions may be executed by a processor to cause a series of operational steps to be performed by the processor to produce a computer implemented process. The computer program instructions may also cause at least some of the operational steps to be performed in parallel. Moreover, some of the steps may also be performed across more than one processor, such as might arise in a multi-processor computer system. In addition, one or more processes may also be performed concurrently with other processes, or even in a different sequence than illustrated without departing from the scope or spirit of the invention.

The computer program instructions can be stored on any suitable computer-readable medium including, but not limited to, RAM, ROM, EEPROM, flash memory or other memory technology, CD-ROM, digital versatile disks ("DVD") or other optical storage, magnetic cassettes, magnetic tape, magnetic disk storage or other magnetic storage devices, or any other medium which can be used to store the desired information and which can be accessed by a computing device.

The above specification, examples and data provide a description of the manufacture and use of the composition of the invention. Since many embodiments of the invention can be made without departing from the spirit and scope of the invention, the invention also resides in the claims hereinafter appended.

What is claimed as new and desired to be protected by Letters Patent of the United States is:

1. A system for identifying portions of a body in which electrical stimulation of that portion of the body to treat a condition or disorder affects at least one of at least one symptom of the condition or disorder, stimulation effect, or side effect, the system comprising:
a computer processor configured and arranged to perform the following acts:
obtaining, for each of a plurality of stimulation instances, an estimation of a region of the body stimulated during the stimulation instance and a score for each of at least one symptom of the condition or disorder, stimulation effect, or stimulation side effect;
determining, for each of a plurality of portions of the body using the scores and the estimates in a permutation test, a likelihood that stimulation of that portion of the body affects at least one symptom of the condition or disorder, stimulation effect, or stimulation side effect; and
storing or displaying the determined likelihoods to identify which portions of the body, when electrically stimulated, affect the at least one of the at least one symptom of the condition or disorder, stimulation effect, or stimulation side effect.

2. The system of claim 1, wherein the acts further include obtaining the plurality of stimulation instances and, for each stimulation instance, a set of stimulation parameters.

3. The system of claim 1, wherein obtaining an estimation of a region of the body stimulated during the stimulation instance comprises estimating the region of the body stimulated during the stimulation instance based on stimulation parameters used during the stimulation instance.

4. The system of claim 1, wherein determining a likelihood comprises forming a matrix for a selected portion of the body and for a selected symptom of the condition or disorder, stimulation effect, or stimulation side effect, the matrix comprising a plurality of rows and columns, wherein one of the columns or rows corresponds to each stimulation instance, wherein, for each of a plurality of the stimulation instances, a first entry in a column or row indicates whether the selected portion of the body is stimulated in that stimulation instance and a second entry in the column or row corresponds to the score for the selected symptom of the condition or disorder, stimulation effect, or side effect for that stimulation instance.

5. The system of claim 4, wherein determining a likelihood further comprises determining a likelihood that a null hypothesis is invalid, wherein the null hypothesis is that the selected portion of the body does not influence the scores for the selected symptom of the condition or disorder, stimulation effect, or side effect.

6. The system of claim 4, wherein determining a likelihood further comprises determining a difference between scores where the selected portion of the body is stimulated and scores where the selected portion of the body is not stimulated.

7. The system of claim 6, wherein determining a likelihood further comprises randomizing the second entries with respect to the first entries to form a plurality of additional matrices.

8. The system of claim 7, wherein determining a likelihood further comprises generating a distribution based on the matrix and the plurality of additional matrices.

9. The system of claim 2, wherein obtaining the plurality of stimulation instances comprises obtaining the plurality of stimulation instances from a plurality of patients.

* * * * *